(12) United States Patent
Graves et al.

(10) Patent No.: US 8,050,939 B2
(45) Date of Patent: Nov. 1, 2011

(54) METHODS AND SYSTEMS FOR USE IN THE PROVISION OF SERVICES IN AN INSTITUTIONAL SETTING SUCH AS A HEALTHCARE FACILITY

(75) Inventors: Alan Graves, Kanata (CA); Brian Vezza, Allen, TX (US); Thomas Chmara, Richmond (CA); John Watkins, Ottawa (CA); Jeffrey Fitchett, Kanata (CA)

(73) Assignee: Avaya Inc., Basking Ridge, NJ (US)

( * ) Notice: Subject to any disclaimer, the term of this patent is extended or adjusted under 35 U.S.C. 154(b) by 981 days.

(21) Appl. No.: 12/003,206

(22) Filed: Dec. 20, 2007

(65) Prior Publication Data

US 2008/0169927 A1    Jul. 17, 2008

Related U.S. Application Data

(63) Continuation-in-part of application No. 11/065,047, filed on Feb. 25, 2005, now Pat. No. 7,676,380, application No. 12/003,206.

(60) Provisional application No. 60/651,623, filed on Feb. 11, 2005, provisional application No. 60/963,695, filed on Aug. 7, 2007.

(51) Int. Cl.
*G06Q 50/00* (2006.01)
(52) U.S. Cl. ......................................................... 705/2
(58) Field of Classification Search ........................ None
See application file for complete search history.

(56) References Cited

U.S. PATENT DOCUMENTS

| | | |
|---|---|---|
| 4,601,064 A | 7/1986 | Shipley |
| 5,291,399 A | 3/1994 | Chaco |
| 5,434,775 A | 7/1995 | Sims et al. |
| 5,465,082 A | 11/1995 | Chaco |
| 5,534,851 A | 7/1996 | Russek |
| 5,544,661 A | 8/1996 | Davis et al. |
| 5,594,786 A | 1/1997 | Chaco et al. |
| 5,610,596 A | 3/1997 | Petitclerc |
| 5,689,229 A | 11/1997 | Chaco et al. |

(Continued)

FOREIGN PATENT DOCUMENTS

CA    2263428    2/1998

(Continued)

OTHER PUBLICATIONS

Jonathan Collins, RFID Remedy for Medical Errors, RFID Journal, http://www.rfidjournal.com/article/view/961, May 28, 2004, 3 pages.

(Continued)

*Primary Examiner* — Brandon Hoffman

(57) ABSTRACT

A system for more optimally providing a service, such as a communications service, in an institutional setting by use of smart context-aware approaches. The system comprises an environmental context processing engine configured to transform sensed data indicative of activity relevant to provision of said service into data indicative of an environmental context in which said activity is deemed to have occurred; a situational context processing engine configured to transform the data indicative of the environmental context into data indicative of a situational context in which said activity is deemed to have occurred; and a decision making engine configured to apply data indicative of an institutional context to the data indicative of the situational context in order to determine an action to be taken in accordance with provision of said service.

49 Claims, 24 Drawing Sheets

U.S. PATENT DOCUMENTS

| | | |
|---|---|---|
| 5,822,544 A | 10/1998 | Chaco et al. |
| 5,877,675 A | 3/1999 | Rebstock et al. |
| 5,901,172 A | 5/1999 | Fontana et al. |
| 5,910,776 A | 6/1999 | Black |
| 5,911,687 A | 6/1999 | Sato et al. |
| 5,942,986 A | 8/1999 | Shabot et al. |
| 5,952,641 A | 9/1999 | Korshun |
| 6,009,333 A | 12/1999 | Chaco |
| 6,026,125 A | 2/2000 | Larrick, Jr. et al. |
| 6,054,950 A | 4/2000 | Fontana |
| 6,211,790 B1 | 4/2001 | Radomsky et al. |
| 6,236,333 B1 | 5/2001 | King |
| 6,239,741 B1 | 5/2001 | Fontana et al. |
| 6,259,355 B1 | 7/2001 | Chaco et al. |
| 6,262,662 B1 | 7/2001 | Back et al. |
| 6,302,844 B1 | 10/2001 | Walker et al. |
| RE37,531 E | 1/2002 | Chaco et al. |
| 6,344,794 B1 | 2/2002 | Ulrich et al. |
| 6,462,656 B2 | 10/2002 | Ulrich et al. |
| 6,539,393 B1 | 3/2003 | Kabala |
| 6,577,238 B1 | 6/2003 | Whitesmith et al. |
| 6,662,068 B1 | 12/2003 | Ghaffari |
| 6,690,741 B1 | 2/2004 | Larrick, Jr. et al. |
| 6,753,671 B1 | 6/2004 | Harvey |
| 6,773,396 B2 | 8/2004 | Flach et al. |
| 6,812,884 B2 | 11/2004 | Richley et al. |
| 6,823,199 B2 | 11/2004 | Gough |
| 6,825,763 B2 | 11/2004 | Ulrich et al. |
| 6,870,916 B2 | 3/2005 | Henrikson et al. |
| 6,876,303 B2 | 4/2005 | Reeder et al. |
| 6,958,677 B1 | 10/2005 | Carter |
| 6,958,706 B2 | 10/2005 | Chaco et al. |
| 6,972,683 B2 | 12/2005 | Lestienne et al. |
| 7,042,337 B2 | 5/2006 | Borders et al. |
| 7,080,061 B2 | 7/2006 | Kabala |
| 7,154,397 B2 | 12/2006 | Zerhusen et al. |
| 7,242,306 B2 | 7/2007 | Wildman et al. |
| 7,283,037 B2 | 10/2007 | Diorio et al. |
| 7,289,227 B2 | 10/2007 | Smetak et al. |
| 7,336,171 B2 | 2/2008 | Kishimoto et al. |
| 2001/0044731 A1 | 11/2001 | Coffman et al. |
| 2002/0044043 A1 | 4/2002 | Chaco et al. |
| 2002/0044059 A1 | 4/2002 | Reeder et al. |
| 2002/0069030 A1 | 6/2002 | Xydis |
| 2002/0147912 A1 | 10/2002 | Shmueli et al. |
| 2002/0165731 A1 | 11/2002 | Dempsey |
| 2002/0183078 A1 | 12/2002 | Hase |
| 2002/0183979 A1 | 12/2002 | Wildman |
| 2003/0055899 A1 | 3/2003 | Burger et al. |
| 2003/0078810 A1 | 4/2003 | Cole et al. |
| 2003/0078811 A1 | 4/2003 | Cole et al. |
| 2003/0132845 A1 | 7/2003 | McDaniel, III |
| 2004/0001446 A1 | 1/2004 | Bhatia et al. |
| 2004/0004460 A1 | 1/2004 | Fitch et al. |
| 2004/0008114 A1 | 1/2004 | Sawyer |
| 2004/0034284 A1 | 2/2004 | Aversano et al. |
| 2004/0078151 A1 | 4/2004 | Aljadeff et al. |
| 2004/0078219 A1 | 4/2004 | Kaylor et al. |
| 2004/0100376 A1 | 5/2004 | Lye et al. |
| 2004/0100377 A1 | 5/2004 | Brackett et al. |
| 2004/0108954 A1 | 6/2004 | Richley et al. |
| 2004/0125938 A1 | 7/2004 | Turcan et al. |
| 2004/0125940 A1 | 7/2004 | Turcan et al. |
| 2004/0145477 A1 | 7/2004 | Easter et al. |
| 2004/0153344 A1 | 8/2004 | Bui et al. |
| 2004/0178947 A1 | 9/2004 | Richley et al. |
| 2004/0186357 A1 | 9/2004 | Soderberg et al. |
| 2004/0193449 A1 | 9/2004 | Wildman et al. |
| 2004/0203930 A1 | 10/2004 | Farchmin et al. |
| 2004/0252015 A1 | 12/2004 | Galperin et al. |
| 2004/0257224 A1 | 12/2004 | Sajkowsky |
| 2005/0017864 A1* | 1/2005 | Tsoukalis ............ 340/539.12 |
| 2005/0027465 A1 | 2/2005 | Pozsgay et al. |
| 2005/0035862 A1 | 2/2005 | Wildman et al. |
| 2005/0105734 A1 | 5/2005 | Buer et al. |
| 2005/0128083 A1 | 6/2005 | Puzio et al. |
| 2005/0148831 A1 | 7/2005 | Shibata et al. |
| 2005/0151641 A1 | 7/2005 | Ulrich et al. |
| 2005/0153681 A1 | 7/2005 | Hanson |
| 2005/0168341 A1 | 8/2005 | Reeder et al. |
| 2005/0188095 A1 | 8/2005 | Gardiner et al. |
| 2005/0201345 A1 | 9/2005 | Williamson |
| 2005/0283382 A1 | 12/2005 | Donoghue et al. |
| 2006/0006999 A1 | 1/2006 | Walczyk et al. |
| 2006/0067250 A1 | 3/2006 | Boyer et al. |
| 2006/0125623 A1 | 6/2006 | Appelt et al. |
| 2006/0143043 A1 | 6/2006 | McCallie, Jr. et al. |
| 2006/0158329 A1 | 7/2006 | Burkley et al. |
| 2006/0282459 A1 | 12/2006 | Kabala |
| 2007/0297589 A1 | 12/2007 | Greischar et al. |

FOREIGN PATENT DOCUMENTS

| | | |
|---|---|---|
| CA | 2362635 | 8/2000 |
| CA | 2373241 | 11/2000 |
| CA | 2434714 | 8/2002 |
| EP | 0 369 662 A2 | 5/1990 |
| EP | 0 973 316 A2 | 1/2000 |
| EP | 1 101 437 A1 | 5/2001 |
| EP | 1 156 336 A1 | 11/2001 |
| EP | 1 536 306 A1 | 6/2005 |
| GB | 2320397 A | 6/1998 |
| GB | 2355889 A | 5/2001 |
| GB | 0602885.6 | 6/2006 |
| GB | 0602887.2 | 6/2006 |
| GB | 0602901.1 | 6/2006 |
| GB | 0602903.7 | 6/2006 |
| GB | 0602904.5 | 6/2006 |
| GB | 0602906.0 | 6/2006 |
| GB | 0602907.8 | 6/2006 |
| JP | 2002157040 A | 5/2002 |
| JP | 2003189359 A | 7/2003 |
| WO | WO 95/01617 | 1/1995 |
| WO | WO9739553 | 10/1997 |
| WO | WO 99/04685 | 2/1999 |
| WO | WO9949378 | 9/1999 |
| WO | WO 99/64974 A1 | 12/1999 |
| WO | WO 00/52498 | 9/2000 |
| WO | WO 2004/032019 A2 | 4/2004 |
| WO | WO 2004/042563 A2 | 5/2004 |
| WO | WO 2004/102457 A2 | 11/2004 |
| WO | WO 2005/043402 A1 | 5/2005 |
| WO | PCT/CA2006/000195 | 5/2006 |
| WO | PCT/CA2006/000196 | 5/2006 |
| WO | PCT/CA2006/000197 | 5/2006 |
| WO | PCT/CA2006/000205 | 5/2006 |
| WO | WO 2006/049728 A1 | 5/2006 |
| WO | PCT/CA2006/000198 | 6/2006 |
| WO | PCT/CA2006/000203 | 6/2006 |
| WO | PCT/CA2006/000204 | 6/2006 |
| WO | PCT/CA2006/001479 | 12/2006 |

OTHER PUBLICATIONS

Claire Swedberg, Ford Deploys RFID-Enabled Chargers, RFID Journal, http://www.rfidjournal.com/article/articleview/1348/1/1/, Jan. 19, 2005, 3 pages.

Parco Merged Media Corporation, "The Parco Real Time Location System", http://www.parcomergedmedia.com/whcs_pgis.html, downloaded Feb. 2005, 5 pages.

Parco Merged Media Corporation, "Improving the Availability of Information", www.parcowireless.com, downloaded Jan. 2005, 8 pages.

Parco Merged Media Corporation, "The Parco Wireless Health Care System (WHCS)", www.parcowireless.com, downloaded Aug. 2004, 8 pages.

Robert J. Fontana, Ph.D., "Experimental results from an ultra wideband precision geolocation system", www.multispectral.com, downloaded Aug. 2004, 9 pages.

Robert J. Fontana et al., "Ultra-wideband precision asset location system", www.multispectral.com, downloaded Aug. 2004, 5 pages.

Robert J. Fontana et al., "Commercialization of an ultra wideband precision asset location system", www.multispectral.com, downloaded Aug. 2004, 5 pages.

Dr. Zeev Weissman, "Indoor Location", Tadlys Ltd., www.tadlys.com, downloaded Jul. 2004, 15 pages.

Chronaki et al, "WebOnCOLL: Medical Collaboration in Regional Healthcare Netwoks", IEEE Transactions on Information Technology in Biomedicine,vol. 1, No. 4, Dec. 1997, pp. 257-269.
Rodriquez et al., "Location-Aware Access to Hospital Information and Services", IEEE Transactions on Information Technology in Biomedicine, vol. 8, No. 4, Dec. 2004, pp. 448-455.
Dongquan, Chen et al., "Wireless local area network in a prehospital environment", BMC Medical Informatics and Decision Making, vol. 4, Aug. 31, 2004, 9 pages.
Office Action mailed on Dec. 4, 2008 in connection with U.S. Appl. No. 11/064,930.
Office Action mailed on Mar. 6, 2009 in connection with U.S. Appl. No. 11/065,396.
Office Action mailed on Mar. 19, 2009 in connection with U.S. Appl. No. 11/065,099.
Office Action mailed on Apr. 1, 2009 in connection with U.S. Appl. No. 11/065,420.
Office Action mailed on Aug. 19, 2008 in connection with U.S. Appl. No. 11/065,047.
Office Action mailed on Oct. 2, 2008 in connection with U.S. Appl. No. 11/065,046.
Office Action mailed on May 16, 2008 in connection with U.S. Appl. No. 11/065,396.
Office Action mailed on Nov. 16, 2009 in connection with U.S. Appl. No. 11/064,930.
Office Action mailed on Jun. 11, 2009 in connection with U.S. Appl. No. 11/064,930.
Office Action mailed on Jun. 12, 2009 in connection with UK Patent Application 0602901.1.
Office Action mailed on Sep. 2, 2009 in connection with U.S. Appl. No. 11/065,071.
Office Action mailed on Sep. 16, 2009 in connection with U.S. Appl. No. 11/303,989.
USPTO Office Action Summary mailed Dec. 17, 2010 in U.S. Appl. No. 11/065,099.

* cited by examiner

FIG. 7N

E8 – Drug Theft or Tampering Detection

Inputs

Facility Information
- Hospital grid map, zones and usage allocation including Pharmacy coordinates, zone, Drug cart routes, route history, drug storage sites

Clinical
- Clinician ID, Drug ID, quantity (by RFID scan, manual entry), Pharmacist ID, Patient ID

Context
- Clinician role, authentication, authorizations
- Clinician/drug/patient association at administration
- Patient drug history, drug regimen
- Zone boundaries of permitted movement or use
- Drug environmental safety (from drug type and sensed drug environment)

Environment
- Drug cart ID and location
- Drug ID (RFID) on cart or before administering
- Drug location (by RFID reader location)
- Packaged drug quantities in stores, on cart (RFID)
- Sensors – drug cart and drug store environment – possible individual drug package environment – by RFID sensors

Functions

Drug Safety, Security and Environment
- Tracking whereabouts of drugs through the chain from incoming to pharmacy to patient administration
- Protecting drugs from misplacement, theft or being exposed to harmful environmental conditions
- Enabling drug inventory activities
- Supporting safe validation administration procedures

Outputs

- Drug location, inventory
- Alerts for misplaced drugs, unauthorized drug movement
- Alerts for drugs approaching "stale date"/support to properly sequence drug usage
- Alerts for drugs exposed to limit environmental conditions
- Support for validated safe drug administration to patients

| | Equipment Tracking, Location and Condition (R2) | Clinician Point of Care Communications (R5) | Code Blue (E1) – Team Forming Phase | Code Adam (E2) |
|---|---|---|---|---|
| Geography | Campus in-building, one or a few buildings | Campus | Campus in-building, one or a few buildings + 250 yards outdoors | Campus |
| Scale | 100's – 10,000's, 1000's per floor, 100's per AP | 100's – 10,000's, 1000's per floor, 10's per AP | 100's of patients, combination of R2 and R5 | 100's of patients, combination of R2 and R5 |
| Location Precision | Room, 3m Proximity or 20cm for advanced application | Room, 3m Proximity or 20cm for advanced application | Room | Room, Outdoor Coverage |
| Other Sensors | On Medical Equipment | No | No (Biohazards??) | No (Heat??) |
| Volume of Data | Kb/s | Mb/s | Kb/s | Kb/s |
| Message Latency | Second Sub-second for Theft Applications | Seconds (User Satisfaction Driven) | Sub-seconds | Seconds |
| App Availability | Medium – 0.99 to high 0.999 | High – 0.999 | Very High – 0.9999 | High – 0.999 |
| Frequency | Routine – Hundreds a Day | Routine – Continual Usage | 200 per Year for 400 Bed Tertiary Care Hospital | Rare Less than 1 per Year |
| Criticality | Moderate (for Efficiency) | Moderate (for Efficiency) | Mission-Critical | High |
| Mobile Devices | Tag | Phone with Graphic Display, Tables, PDA's | Phone with Graphic Display, Tables, PDA's for EHR | Phone with Graphic Display |

| Privacy | Minimal, For Patient Data in Monitoring Apps | High | Minimal – During Incident | Minimal – During Incident |
|---|---|---|---|---|
| Security (of Application Access) | Medium | High | Medium | Low (Due to Rarity) |
| Auditing, Logging (if Required) | Yes | Yes – Efficiency, Malpractice | Yes – Detailed (?) Hospital May Not Want | Yes |
| Mobile Device Battery | 6 Months Minimum (Tags) | 1 day (Shift plus Personal Time when on Call) 6 Months min (Tags) | 1 Shift 6 Month min (Tags) | 1 Shift 6 Month min (Tags) |
| Data Characteristics | -Location–Periodic Pings -Condition–Low Data Rate Messages -Operational Data–Graphic or Web Pages, Low-res Video such as EKG | -Voice -Text, Image -Video–Collaborative, Diagnostic -Location -Web Pages | -Voice / Audio -Text -Location -Web Pages, e.g. EHR | -Voice / Audio -Text -Location |
| Data Rate | Kb/s | Mb/s | Kb/s | Kb/s |
| Privacy | Minimal, For Patient Data in Monitoring Apps | High | Minimal – During Incident | Minimal – During Incident |

US 8,050,939 B2

METHODS AND SYSTEMS FOR USE IN THE PROVISION OF SERVICES IN AN INSTITUTIONAL SETTING SUCH AS A HEALTHCARE FACILITY

CROSS-REFERENCE TO RELATED APPLICATIONS

The present application claims the benefit of U.S. Provisional Patent Application Ser. No. 60/963,695, filed on Aug. 7, 2007, incorporated by reference herein.

The present application is also a Continuation-in-Part of U.S. patent application Ser. No. 11/065,047 to Graves et al., filed on Feb. 25, 2005, now U.S. Pat. No. 7,676,380, incorporated by reference herein, which claims the benefit of U.S. Provisional Patent Application Ser. No. 60/651,623, filed on Feb. 11, 2005, also incorporated by reference herein.

FIELD OF THE INVENTION

The present invention relates generally to methods and systems for use in the provision of services in an institutional setting such as a healthcare facility.

BACKGROUND

An institutional setting, such as a healthcare facility, may have a very complex structure. Typically, a large amount of physical and human resources are relied upon to provide a wide variety of services, including clinical as well as non-clinical services, both routine and emergency.

To address the evolving needs of the healthcare facility, various customized systems have been implemented over the years to deliver services on an individual basis. However, this service-specific approach comes at a high cost of installation and maintenance. In addition, as greater numbers of service-specific systems are installed alongside and on top of one another, the distribution and usage of physical and human resources in the healthcare facility becomes sub-optimal, to the point where it may well fall below mission-critical standards. Some of the issues include a multiplicity of differing infrastructures, differing and non-coordinated Human-Machine interfaces, both at the user level and at the IT-management level, lack of integration between systems and inability to move information between disparate systems. This situation is undesirable and, should it occur, may negatively taint a clinician's experience as well as the usability of the technology and lead the clinician to reject rather than embrace future technological advancement, despite its lifesaving potential.

Thus, there is a need in the industry to develop a system that enables the provision of a wide range of services in an institutional setting such as a healthcare facility without the drawbacks of conventional service-specific solutions.

SUMMARY OF THE INVENTION

According to a first broad aspect, the present invention seeks to provide a system for more optimally providing a service, such as a communications service, in an institutional setting by use of smart context-aware approaches. The system comprises an environmental context processing engine configured to transform sensed data indicative of activity relevant to provision of said service into data indicative of an environmental context in which said activity is deemed to have occurred; a situational context processing engine configured to transform the data indicative of the environmental context into data indicative of a situational context in which said activity is deemed to have occurred; and a decision making engine configured to apply data indicative of an institutional context to the data indicative of the situational context in order to determine an action to be taken in accordance with provision of said service.

According to a second broad aspect, the present invention seeks to provide a method for providing a service in an institutional setting. The method comprises obtaining sensed data indicative of activity relevant to provision of said service; transforming said sensed data into data indicative of an environmental context in which said activity is deemed to have occurred; transforming the data indicative of the environmental context into data indicative of a situational context in which said activity is deemed to have occurred; and applying data indicative of an institutional context to the data indicative of the situational context in order to determine an action to be taken in accordance with provision of said service.

According to a third broad aspect, the present invention seeks to provide a system for providing a service in an institutional setting. The system comprises means for obtaining sensed data indicative of activity relevant to provision of said service; means for transforming said sensed data into data indicative of an environmental context in which said activity is deemed to have occurred; means for transforming the data indicative of the environmental context into data indicative of a situational context in which said activity is deemed to have occurred; and means for applying data indicative of an institutional context to the data indicative of the situational context in order to determine an action to be taken in accordance with provision of said service.

According to a fourth broad aspect, the present invention seeks to provide a method, comprising detecting a situation occurring in a clinical workflow; and modifying communications to and from the workflow based on the detected situation.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the accompanying drawings:

FIG. 8 is a table showing example quantitative requirements for four example services.

DETAILED DESCRIPTION

Figure 1:
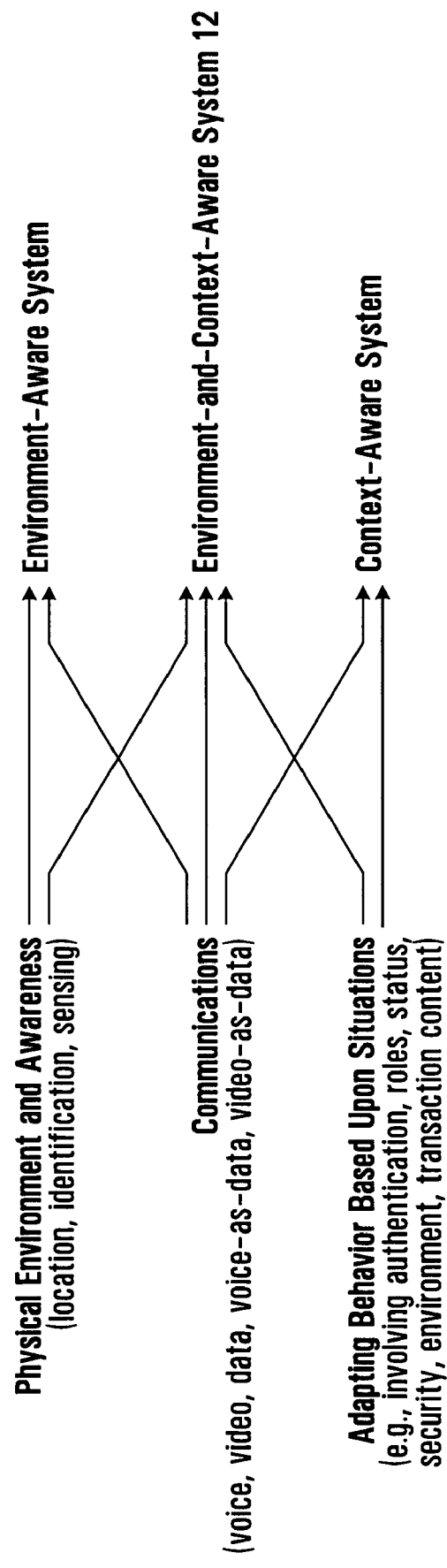
FIG. 1 conceptually illustrates an environment- and context-aware system for providing services in an institutional setting, in accordance with a non-limiting embodiment of the present invention.

In accordance with non-limiting embodiments of the present invention, and with reference to FIG. 1, there is provided an Environment- and Context-Aware System (ECAS) 12 with application to a healthcare facility. The ECAS 12 utilizes an arrangement of sensors, a communication system as well as access to information from configuration servers, policy servers, user lists and profiles, institution information and roles information in order to render significant and useful decisions concerning the provision of services within the healthcare facility. Specifically, the ECAS 12 enables decisions to be made regarding what actions should be taken that are consistent with a particular service, when certain "situations" are deemed to occur, based on sensed data relating to the particular service.

In accordance with a non-limiting example, a "situation" can be viewed as a state of affairs or combination of circumstances, the aggregate of multiple appropriate factors acting on an individual or group to condition behavioral or clinical workflow-related patterns or expectations of patterns.

The sensed data may be the result of location/proximity sensing technology and/or or forms of physical world sensors (e.g. optical, thermal, video, pressure, gas, toxin and biotoxin, vibration/movement, acoustic, various clinical/other specialized and other types of environment-plane sensors). The ECAS 12 can also take into account the status or condition of the communication system itself. In accordance with one non-limiting example, the totality of the "environment" (including locational aspects, thermal aspects, humidity aspects, radiation aspects, etc.) is separated into "planes", the contours of which can be measured by sensors active in that plane. Thus, as will be seen later one, the contours between planes can be combined to deduce "plane-rich" perspectives, which is a heightened environmental awareness.

The decisions taken by the ECAS 12 can result in adaptation or optimization of communications taking place in the communication system, which may or may not be to such an extent as to enable improved, enhanced or even new clinical workflows and processes to result. This may mean preferentially feeding appropriate information to an authenticated user (including information determined to be relevant to the user's situation), preventing communications to an inappropriate user, adapting communications to the circumstances of the user or the user equipment, establishing machine-to-machine communication with unattended equipment, initiating communications when certain circumstances arise, and so on.

In this manner, the ECAS 12 can provide adaptive, smart communications, based upon environmental awareness on plural environment-planes (including personnel and equipment location, identity, proximities, physical environments, etc.) and deduced situations. This is combined with an ability to access permissions and authorization/authentication profiles for actual or prospective users (human or machine) as well as other databases including policy databases. Thus, services can be provided that adapt to the actual communications needs of legitimate users in the context of both the environment in which they operate and their clinical workflow situation.

Figure 2:
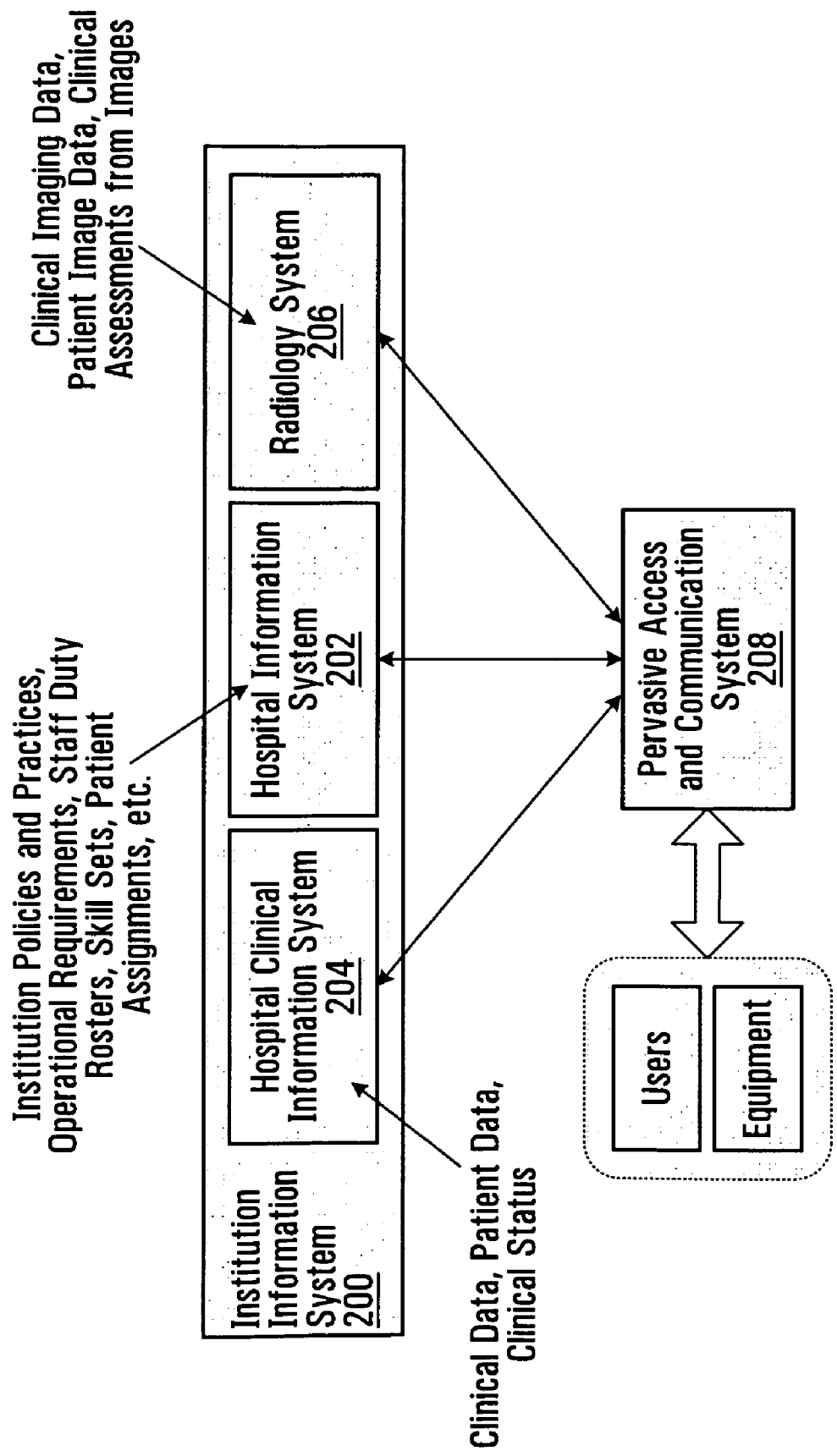
FIG. 2 shows various component features of a healthcare facility.

Reference is now made to FIG. 2, which shows a healthcare facility such as a hospital, campus or other architectural arrangement. The healthcare facility has a number of component systems, including an institution information system 200 and a pervasive access and communication system 208. The institution information system 200 comprises a healthcare information system (HIS) 202, a healthcare clinical information system (HCIS) 204, a radiology system 206. Each of these systems is now described in some detail.

The HIS 202 may comprise databases for storing a variety of data, examples of which include general institution data, such as financial data, building maintenance schedules, and so on. The HIS 202 may also comprise databases for storing information about which clinicians are accredited, what their rights and privileges are, their work schedule and preferences including their IT preferences, etc. The databases in the HIS 202 may also contain information about other healthcare facility support staff, such as orderlies, maintenance staff, administrative staff, or biomedical engineers. The databases in the HIS 202 may also contain information about visiting clinicians who have approval to work in the healthcare facility, yet are not formally part of the facility's staff. In this sense, the databases in the HIS 202 can contain information on dynamic/interim users, data, rights and privileges, as well as more formal and more permanent users, data, rights and privileges. The databases in the HIS 202 do not contain clinical information about the patient base although they may contain non-clinical data about the patient base.

The HCIS 204 may include the following sub-components:
- a healthcare clinical information system (HCIS) core, which links and supports the clinical databases of multiple departments and databases;
- departmental systems, many of which will have been acquired as stand-alone functions and which will have had to have been subsequently integrated together;
- local Electronic Health Records (EHRs—or Electronic Patient Records (EPRs)) for patients in the healthcare facility or who have been treated by the healthcare facility;
- test laboratory IT systems and databases with their different functions, modalities and outputs;
- firewalled secure gateways out to other locations for connectivity to centralized business continuity/disaster recovery (BC/DR), remote centralized EHR, etc.

The above sub-components may comprise databases for storing a variety of data, examples of which include:
- policies (which define the responses to be taken under various situations and for various services in order to achieve desired results);
- lists of entities (such as doctors, nurses, medical equipment) and associated IDs and AAA information;
- patient medical status;
- patient test data;
- patient schedule data;
- patient-clinician association data;
- EHR data;
- EPR data;
- EMR data (clinic-based applications)
- ordered patient treatment data;
- diagnosis data;
- prognosis data;
- staff skills lists; and
- duty rosters.

The above is a non-exhaustive list, as other possibilities remain, and are within the scope of the present invention. The databases in the HCIS 204 could also store policies which describe minimal and optimal combinations of resources (including people, machines, data, network, etc.) to perform certain functions. For example, the formation of a "Code Blue" team requires certain clinicians and equipment to be reserved within a severely limited time to try and save a patient's life. Other "code names" have their own requirements as well as other processes. It should be appreciated that although the "code names" vary between clinical jurisdictions, a healthcare facility's underlying need for the associated services does not. The names used here are those used in the Doctors Hospital, Columbus, Ohio.

The radiology system 206 comprises a suite of non-visible light imaging modalities, such as X-ray, Magnetic Resonance Imaging (MRI), Computed Tomography (CT) scan, Positron Emission Tomography (PET)-scan as well as a Radiology Information System (RIS) which may include a Picture Archiving and Communication System (PACS) to move imaging data between modalities and diagnostic terminals and radiologists as well as archiving and accessing information stored in a radiology information database.

The pervasive access and communication system 208 provides access and communication capabilities throughout the healthcare facility. This can be achieved by one or more of the following individual sub-networks:

voice network;

data network;

converged multimedia network: may use VoIP soft switches to provide voice services, which in turn provides more opportunity for communication sessions via SIP;

regional and metro networks: many healthcare facilities have regional operating entities or fall under common administration. Thus, there can be an inter-institutional metropolitan network, which may consist of high-capacity fiber links between healthcare facilities and data centers, for the purposes of data storage, PACS and health records systems, disaster recovery, voice communications, etc. The metropolitan network also allows the healthcare facilities to communicate with EMS and city services;

video conferencing and telemedicine network: a specialized infrastructure may exist to support video conferencing and telemedicine systems requiring higher resolution and/or time-sensitive performance;

wireless network: an example of a wireless local area network (WLAN) for voice and data point-of care applications. WLAN-capable user equipment integrate with, for example, nurse call systems which send informative text to the WLAN-capable user equipment as the nurse is being called. Other examples include cell phones or smart phones, which can be used for scheduling and contact in the WLAN;

legacy paging system;

equipment monitoring network: some equipment uses legacy 802.11 standards for point-to-point communications (e.g. wireless EKG monitors). Equipment such as infusion pumps may or may not contain an 802.11 WLAN communications capability; and clinical and virtual private network (VPN) access: satellite clinics access the HIS 202 and HCIS 204 via T1, digital subscriber line (DSL), or VPN. For remote clinicians, such as outpatient nurses, personal VPN access over the cellular data network can be used.

The above is a non-exhaustive list, as other possibilities remain, and are within the scope of the present invention.

Figure 3:
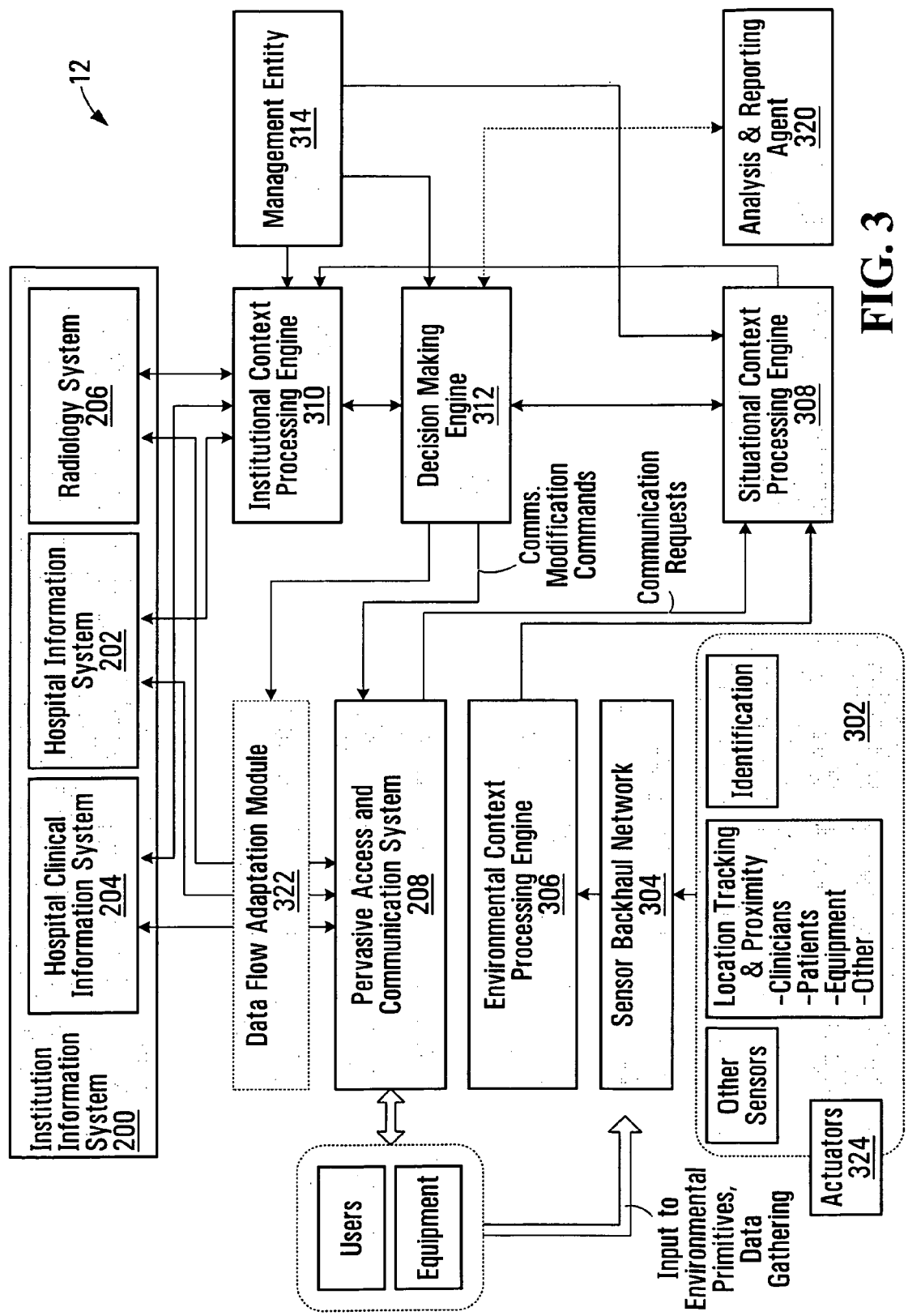
FIG. 3 shows various component features of a healthcare facility that includes an environment- and context-aware system.

Reference is now made to FIG. 3, which shows the healthcare facility of FIG. 2, enhanced with the addition of a number of component systems, including a sensor arrangement 302, a sensor backhaul network 304, an environmental context processing engine 306, a situational context processing engine 308, an institutional context processing engine 310 and a decision making engine 312. Each of these systems, which can be implemented using hardware, software, firmware, control logic or a combination thereof, is described below in some detail. It should be appreciated that the context processing engines 306, 308, 310 can be configured and/or reconfigured via one or more management entities 314, such as consoles or terminals for example. Specifically, the management entities 314 could be accessed by users (such as system administrators) to input algorithms and/or rules that specify the operation of the processing engines 306, 308, 310.

Figure 4:
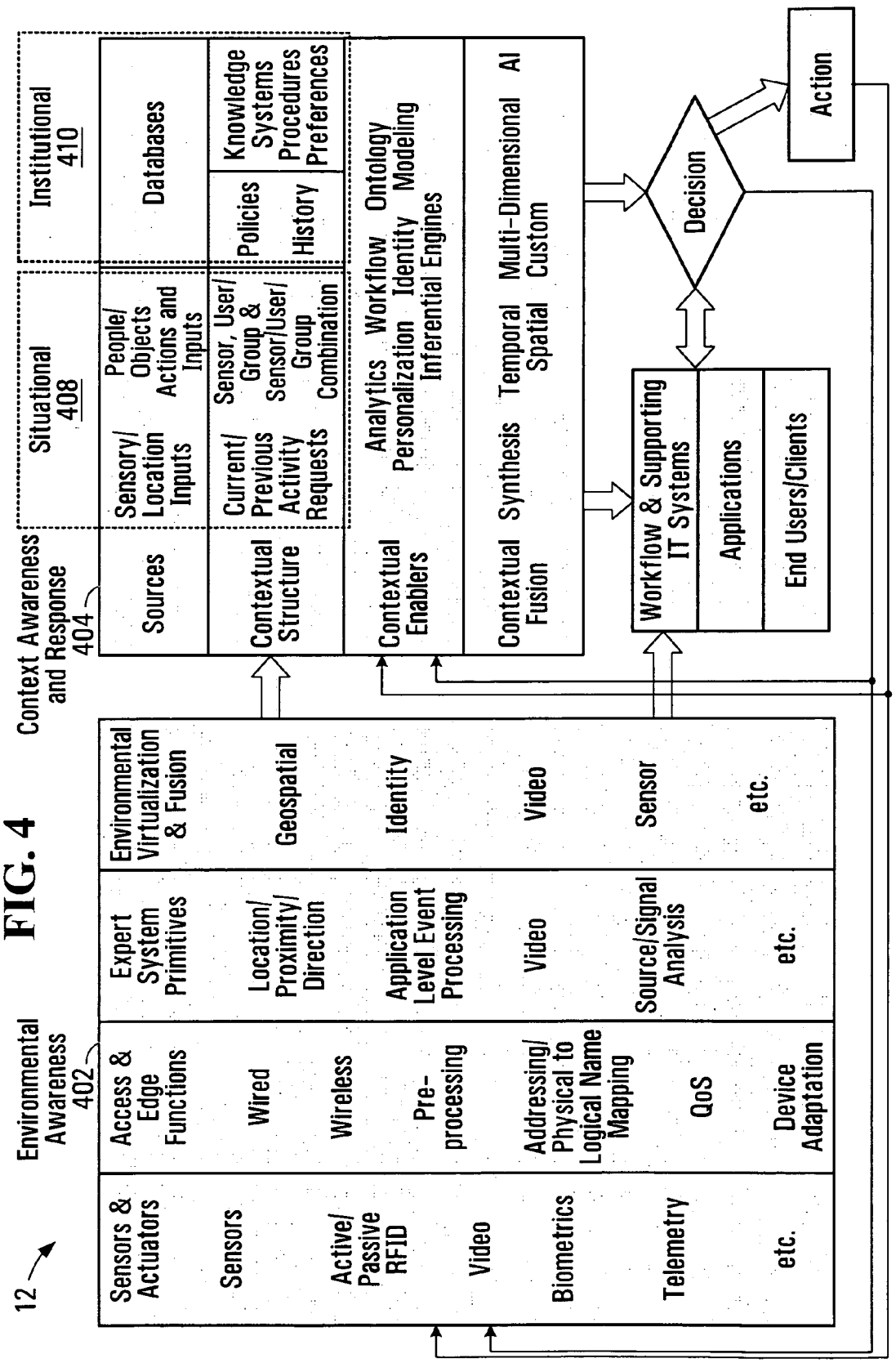
FIG. 4 depicts at a high level an environmental awareness component and a contextual awareness and response component of the environment- and context-aware system, in accordance with a non-limiting embodiment of the present invention.

Before describing the various building blocks of FIG. 3 in more detail, reference is now made to FIG. 4, which provides a high level view of an "Environmental Awareness" component 402 and a "Contextual Awareness and Response" component 404 of the ECAS 12.

The Environmental Awareness component 402, which can be implemented by the environmental context processing engine 306, enables a comprehensive understanding of the environment in which a user, object or other entity operates, by collecting data from various sensors, detectors, location markers, identifiers and the like, bringing this data to a point where data reduction can be applied, whereby it can be logically mapped and correlated and expert system primitives can be derived allowing the detection of various conditions (e.g. proximity of a clinician with his allocated patient) and data useful to the situational context processing engine 308 can be formulated. In a healthcare facility, this could include a wide range of sensors (e.g. radiation, video, temperature, RFD tags, patient monitoring and vital signs, etc.). By collecting, processing, aggregating, fusing, and virtualizing this information, a much deeper understanding can be created. This heightened awareness is beneficial on its own merits as an independent functional block for use by other systems and applications. It can also be useful to integrate the result of the "Environmental Awareness" component 402 into the Contextual Awareness and Response component 404.

Specifically, the Contextual Awareness and Response component 404 has two parts, namely a situational part 408 (which can be implemented by the situational context processing engine 308) and an institutional part 410 (which can be implemented by the institutional context processing engine 310). In one non-limiting example, situational context can be viewed as the situation or circumstances surrounding an event, the previous history of that event and associated actual factors in substantially real time, while institutional context can be viewed as the context of what the institution's or facility's policies, procedures and the like would indicate ought to be happening. For instance, a situational context might have Dr. Jones administering CPR to Mrs. Smith—the institutional context might declare that Dr Jones normally should not be treating Mrs. Smith but, since a "Code Blue" has been declared and Dr. Jones is "Code Blue certified" he can have full access to Mrs. Smith's records. As a whole, the Contextual Awareness and Response component 404 takes raw information, databases, Environmental Awareness information and other types of "inputs" and melds this into domain- and/or situationally appropriate awareness and responses. To this end, the Contextual Awareness and Response component 404 may implement contextual fusion (such as synthesis, artificial intelligence, spatial, temporal, multi-dimensional and customized fusion) based on contextual enablers (such as analytics, modeling, personalization, workflow, ontology, identity and inferential engines).

In a very simple example, "Presence" information can be used by clinicians to indicate their availability to communicate with others. In a more useful and powerful example, the Context Awareness and Response component 404 could determine which clinicians are on duty, are available for routine or emergency level communications, their location, area of expertise, etc., in order to understand their situational context, as would be done by the situational context processing engine 308. This view can be integrated with the overall policies, procedures, preferences, and systems of their company or department which is also known as "Institutional" context and is provided by the institutional context processing engine 310.

The combination of both Environmental Awareness (i.e., the environmental context processing engine 306) and Contextual Awareness and Response (i.e., the situational context processing engine 308 and the institutional context processing engine 310), enables a comprehensive understanding of conditions and provides the ability to leverage that understanding to make decisions and take actions by a wide range of workflow and supporting IT systems, applications, and end users or their clients. Ultimately, for a fully featured real-life system there will be a number of policy inputs, decision points, and feedback mechanisms to fine tune, adapt, and evolve based on changing conditions, inputs and strategies.

Turning now to the specific ECAS building blocks in FIG. 3, the sensor arrangement 302 includes sensors for collecting data about each of the environment-planes. These can be designed to include physical sensing capabilities, electromagnetic transponders and other data-gathering capabilities to interface with various environments.

A non-exhaustive list of possible sensors is provided herein below:
  location, tracking and proximity sensors: active and passive;
  cameras: movement detection and object identification using picture and video or processed derivations of components therein;
  clinical sensors including stand-alone, on-body, in-body (ingestible or implanted) and on-equipment sensors;
  sound sensors: voices, mechanical sounds, sounds from movement;
  vibration sensors: fence vibrations, ground vibrations from intrude inadvertent interaction;
  movement sensors: motion sensors, contact openings, closings, e.g., on gates, entry points;
  visible light sensors: video surveillance (manual or automatic analysis), photobeam disruption;
  infra-red light sensors: video surveillance (manual or automatic analysis), photobeam disruption, changes in reflected energy, self-radiation (hot persons, objects);
  wireless signals: interaction of objects, personnel with RF fields (quasi-radar or interferometric), active RF emissions (inadvertent/clandestine or deliberate/IFF);
  mass/weight/pressure sensors: ground perimeter pressure sensors for personnel, objects with significant mass, matching mass to expected mass;
  chemical sensors: chemical trace analysis, explosives detection;
  biotoxin sensors: airborne, surface bacteria, virus sensing;
  hard radiation sensors: Geiger counter/detection of nuclear decay, hidden object sensing (X-ray, nuclear scanners);
  liquids/fluids/water sensors: fluid sensors/floats, humidity sensing; and
  gas/vapour sensors: hazardous gas detection (e.g., $H_2S$ sensor, CO sensor or sensors for more problematic gases).

The above is a non-exhaustive list, as other possibilities remain, and are within the scope of the present invention.

The above sensors can be generally classified in accordance with the following functions:

Patient Monitoring

Sensors suitable for the ECAS 12 additionally include a wide variety of patient monitoring sensors. In contrast to patient monitoring sensors that are deployed in closed monitoring systems, clinical data sensed by such patient monitoring sensors can be transmitted over the pervasive access and communication system 208 if the latter is equipped with sufficient security. Such clinical data can be used by the environmental context processing engine 306 and the situational context processing engine 308, and can be archived in, for example, a suitable EHR or EPR. In this case not only can medical instruments that control and monitor a particular patient monitoring sensor be networked and have the ability to be monitored and control via management systems running on a common IP infrastructure, but also can the medical data itself.

Building

The include door alarms, fire, bio-toxins, and gas.

Inventory

These include heat, humidity, and light. These are useful for light-sensitive, heat-sensitive or humidity-sensitive drug and medical supplies such as stents.

Location tracking and proximity sensors are also useful in inventory applications, and these are described further below.

Security

These include door alarms, motion sensors, and biometrics for building (e.g. video/facial) and device (e.g. fingerprint) security.

Location Tracking and Proximity

Location tracking and proximity systems for indoor use range in precision from centimeters to tens of meters. The percent of measurement samples within a given precision giving rise to the system accuracy is a consideration of service requirements. Certain WLAN systems show a precision of 6 meters for a 90% accuracy level. This is sufficient for some healthcare services, such as coarse equipment tracking and determining which ward a clinician is in, but not others, for example clinician-terminal or clinician-patient association. For these services a high precision location system or a proximity system may be more suitable—and there are several tradeoffs, benefits and drawbacks to consider when selecting which way to proceed. Latency, coverage, and security are also important to varying degree for different services.

Implicitly most location systems include an identification component; however there are examples where this need not be true. Thermal or video imaging systems, for example, could alert monitoring system to the location of a general object. In healthcare, these may be useful in specialized circumstances or in specific areas of the healthcare facility. They are relevant to security services.

WLAN, RFID or other wireless tags can also store information about prior life, i.e., they can contain elements of sensor behavior. WLAN tags can also contain motion sensors.

Integrated humidity sensors may be used for medical supply inventory services. Outdoor locations systems and integration with indoor systems also have healthcare applications. These include Assisted Global Positioning System (A-GPS), and cellular triangulation.

Non-limiting examples of location tracking and proximity systems for in-building healthcare include:

WLAN Tags

WLAN tags are typically on the order of 5×7 cm in size, with system accuracy on the order of less than 5 meters. Wireless computing devices (PDA, tablets) can also be located via the use of soft clients or passive detection. The accuracy of WLAN location technology is sufficient for coarse equipment tracking and inventory services, a common demand in healthcare. WLAN location implementations do not require additional infrastructure initially, i.e. above that used for communications. WLAN tags currently are used for high value inventory items, largely due to their relatively high cost. The range of these systems makes them suitable to track equipment moving throughout the healthcare facility to approximately a room-level resolution. Suitable example WLAN systems are based on RF fingerprinting.

The function of a WLAN tag can also be integrated in software that is run by WLAN-capable computing devices such as laptops or phones. WLAN-capable devices without the intentionally system-visible tagging function can be detected by purpose-based sensors that are deployed for security reasons to detect and located rogue WLAN clients.

Ultra-Wide Band (UWB) Tags

Systems based on UWB tags offer increased accuracy, down to tens of centimeters or less, but at the cost of additional wireless infrastructure. UWB tags can be as small as less than about 3 cc (2.5 cm×1.5 cm×0.7 cm) in volume and also employee badge shaped tags are available both with and without a biometric scanner (for fingerprints). The accuracy of UWB tags permits an expanded range of applications, such as associating a phone or portable computer terminal with a person near it, or two people together such as a clinician and a patient. UWB systems are typically based on time-difference multi-angulation or time-difference-of-arrival.

Optical and Acoustic

Optical (infrared) systems are legacy systems. Acoustic systems have the advantage of no RF interference, which can be advantageous when considering the setting of a healthcare facility.

RFID and Proximity

Proximity solutions are based on various classes of RFID. Passive RFID tags can be used for drug tracking and security badges in healthcare facilities. RFID tags have the advantage of no battery (passive tags—except when activated) or low power consumption (battery powered Class II-IV tags). Their range can vary significantly, but for passive tags likely to be used in healthcare facilities that range is on the order of a few meters. The passive RFID tags require a reader nearby, which may be incorporated in a communications device such as an IP phone. Thus, the RFID tags could be used to detect the proximity of owner to the device or to configure the device for the owner of the tag. The low cost and short range of passive RFID tags make them attractive for higher quantity, low value inventory services. RFIDs uses unlicensed RF frequencies for their operation, and are typically activated in a transponder-like manner by an RF activation and powering signal.

The above sensors may be passive or active devices. For instance a transmitting UWB tag and a set of location triangulation receivers make up a location sensing function by use of active technology, while a simple thermocouple can make a passive temperature difference sensor (although in this case this could be combined with an active digitization and transmission function to backhaul the thermocouple output voltage values). A simple door closure contact switch is another example of a passive device.

The sensors may also include a geographical and time component within the monitoring system, although there are exceptions (e.g., a group of sensors could theoretically determine its own location, or time reference in relation to other events).

The sensor arrangement 302 may also include actuators coupled to the above-mentioned sensors and having controllable functions. For example, an actuator coupled to a particular sensor may provide the ability to turn the particular sensor on or off, initiate a self-test with the particular sensor, or cause a physical effect such as opening or closing a door lock. Individual sensors and actuators may be integrated devices or separate but connected devices.

Associated actuator pairing may exist for each sensor. For example, a door lock actuator may be paired with a door alarm sensor or vice versa. Moreover, motion detectors on WLAN tags can also contain actuators such as flashing light and sounds. Still other possibilities exist and are within the scope of the present invention.

The sensor backhaul network 304 back-hauls the sensed data from the sensor arrangement 302 to the environmental context processing engine 306. The sensor backhaul network 304 may rely on wired or wireless backhaul. Wired backhaul is generally more dependable but is expensive to install and is often geographically limiting unless the sensor density is low. Both wired and wireless can now offer exceptionally high levels of security. Wireless backhaul is more convenient and can be cheaper but raises issues of the quality and dependability of the RF channel as well as the powering of the sensor node, since powering it over a (presumed non-existent) wired infrastructure may not be an option. Wireless access methods include WLAN, ZigBee (IEEE 802.15.4), and Bluetooth. WLAN has been described above. Lighter weight protocols such as ZigBee have emerged for other sensors because of the requirement for low-cost and low power, coupled with the fact that sensors do not always require a full communications protocol stack. Another method of wireless access, for example for body monitoring sensors, is via Bluetooth or proprietary wireless connections to a wired or wireless terminal. The terminal may contain storage and processing, and has a connection to the environmental context processing engine 306 via the sensor backhaul network 304. This approach may be useful for home and outpatient care.

The sensor data gathered by the sensor arrangement 302 and arriving via the sensor backhaul network 304 is processed by the environmental context processing engine 306 to extract useful information. For instance a single UWB receiver output cannot provide the location of a transmitting tag, other than it is somewhere within range of the UWB receiver. However, in the case of a localization function, combining the measurements from multiple (e.g., 3 or more) location receivers allows the location of the tag in 2-D or 3-D space to be pinpointed within a few centimeters of its actual location.

To this end, and with reference again to FIG. 4, which shows the functions performed between the various processing engines, the environmental context processing engine 306 may be configured to perform the following:

- edge functions. These include sensor collection, processing, and encapsulation functions performed at the edge of an IP network. These may also include QoS processing, priority tagging, real-time control, filtering, and content pre-processing; and
- sensor system virtualization. This includes creating common representations (templates) of the sensed data. This also includes processing and amalgamation of lower-level data.

The above is a non-exhaustive list, as other possibilities remain and are within the scope of the present invention.

By way of a specific non-limiting example, the environmental context processing engine 306 may implement simple functions such as detecting activity of a basic environmental parameter relevant to a simple service provided in or by the healthcare facility, such as monitoring location or temperature. By way of another specific non-limiting example in relation to a more complex service provided in or by the healthcare facility, the environmental context processing engine 306 may provide a sophisticated, precise ability to calibrate and relate the activity in or across multiple environments or factors such as location/proximity, temperature, pressure, radiation levels and types, the presence of various hazards (smoke, toxic gases or chemicals, harmful radiation, bio-toxins, etc.). In either case, the environmental context processing engine 306 transforms the sensed data into data indicative of an environmental context in which the activity is deemed to occur.

Often it is useful to compare, correlate, or review the extracted information from one sensor with that from other sensors, either or both operating in the same environment-plane or in other environment-planes, in order to make a situational determination. This is the responsibility of the situational context processing engine 308. Specifically, the output of the environmental context processing engine 306 (i.e., the data indicative of the environmental context) is fed to the situational context processing engine 308 along with other inputs, including from the pervasive access and communication system 208 and selected data from the HIS 20, HCIS 204 and radiology system 206. As mentioned above, the data indicative of the environmental context reflects an activity that is considered relevant to a particular service being provided in/by the healthcare facility.

The situational context processing engine 308 is configured to transform the data indicative of the environmental context into data indicative of a "situational context" in which a sensed activity is deemed to have occurred. The situational context can be derived not only from the output of the environmental context processing engine 306 but also from activity of the pervasive access and communication system 208 or of aspects of communications crossing the pervasive access and communication system 208. Specifically, the activity of the pervasive access and communication system 208 may signal any of the following:

Communications Presence

Communications presence is an indication of a willingness and ability to communicate. Basic communications presence tells the situational context processing engine 308 if a given clinician is online or offline and if he/she is active within the pervasive access and communication system 208. Communications presence can be more sophisticated, such as identifying the current level or type of activity, such as "active in a meeting" or "do not disturb—in operating room." Some of this information may be manually input by a user or it could also be derived based on, for example, the duty roster of the surgeon combined with his/her location and perhaps those of other clinicians if it is a complex surgery. It can also include some of the items below, either processed or in raw form:

Device Type and Device Capabilities

This information answers questions such as "is it a PDA or laptop, and does it have a camera?" "What state is the device in?" "What is the current modus operandi?" "What functions can be controlled by the system, e.g., can it be muted?" Clinical mobile devices may require a "privacy" mode.

Bandwidth Usage

This is useful for priority or quality of service requirements.

Service Type and Session Type

This information answers questions such as "is a voice, video, or data session in progress?" "Can it be interrupted for an urgent call, such as a nurse call or emergency Code call?" "What are the required connectivity, network quality and terminal capabilities to successfully deliver this service?"

Entity Status

The nature of this information can be considered from two perspectives. First, where an entity within a system is a machine, "entity state" is the state of the machine. For example the state of a medical instrument: Is the machine operational? Are there any alarms? What is its maintenance status? Second, where a software agent is interacting with a communications system, there are many analogies between "entity state" and "communication presence"; hence the term "entity presence" can be used.

Thus, by combining certain outputs of the environmental context processing engine 306 and the pervasive access and communication system 208, the situational context processing engine 308 determines a "situational context". In one non-limiting example, the situational context can be viewed as a state of affairs or aggregate of multiple appropriate factors allowing the determination or discrimination and interpretation of the potentially significant aspects, parameters surrounding the sensed activity.

As such, the situational context can reflect simple traffic loads and availability of resources or more detailed information such as which users are accessing which classes of information or which users are accessing which servers or even which groups of users are, from a network attachment perspective, in the same general vicinity and what their combined skills would imply might be the situation. The situational context can also be extended to deducing the workflow status or likely workflow status of a particular clinician/patient encounter by examination of the nature, frequency and destination of information flows to and from the clinician, as well as examination of the clinical information being transmitted, assuming that appropriate security and privacy safeguards are in place.

The situational context processing engine 308 produces an output (i.e., data indicative of the situational context) that allows downstream decisions to be made whose relevance/validity increases with the precision and accuracy of environmental characterization data as well as the comprehensiveness of environmental sight. For instance an environmental visibility of only location information is not as useful as having visibility of location, heat profile, toxic gas and smoke distribution and visible or infra-red radiation in a situation where a fire has occurred and the ECAS 12 is responding to that emergency situation.

There is also a need for appropriate levels of precision and accuracy for each situation. Precision and accuracy are not the same thing. For instance to associate a tablet PC with a clinician may mean detecting that the tablet PC is within the personal zone of the physician—which, dependent upon the situation and circumstances, extends for 50-100 cm or even more around him/her, primarily being in front of the clinician. A location system with a precision of +/−160 cm will not work properly because it is too imprecise, whereas one with a precision of +/−10 cm is expected to work adequately. Since the Tablet PC may be used for sensitive data, the situational context engine 308 has to accurately associate the clinician to the tablet PC which means that, if the location system is to be the main determinant of this, it must have a very high accuracy (e.g., 99.99%). For this reason a location or other environmentally derived authentication may form part of an authentication process rather than the whole process. Nevertheless it can radically simplify the rest of the process, thereby reducing user fatigue, and can provide safeguards against the rest of the process making errors. For instance if Dr. Smith is on the $3^{rd}$ floor and suddenly his ID is being used to access the system from the $15^{th}$ floor it is likely that an illegal or illicit activity is under way based upon a stolen, duplicated or misappropriated ID and appropriate safeguards can be taken.

The output of the situational context processing engine 308 (i.e., the data indicative of a situational context) is provided to the decision making engine 312.

The decision making engine 312 is configured to apply an "institutional context" to the data indicative of the situational context in order to determine an action to be taken in accordance with provision of the service. In accordance with a non-limiting example, the institutional context can be viewed as "what the institution anticipates, requires or expects to have happen or to have happened, or has policies and procedures requiring to happen or to have happened, in response to specific or combinational determinations of situational context by the situational context processing engine 308". In a specific scenario, the institutional context can be based on data that is non real-time and input to databases based on institutional policy.

In order to determine which institutional context is relevant to the decision being made by the decision making engine 312, the institutional context processing engine 310 is used. Specifically, the institutional context processing engine 310 interfaces with the HIS 202, HCIS 204 and radiology department 206 via an underlying communications network (not shown), over which raw data and policy frameworks are provided to the decision making engine 312.

The decision making engine 312 implements coordination and processing functions, associated with a set of policies, which makes context decisions and adapts the behaviour of the pervasive access and communications network 208, for each service being provided. To this end, the decision making engine 312 can implement one or more rules engines.

One example of a possible outcome of the decision making engine 312 is a decision to effect a communication action, either directly or by sending instructions to the pervasive access and communication system 208 to effect that communication action. A data flow adaptation module 322 (shown in FIG. 3) could be provided in the pervasive access and communication system 208 for that purpose.

By way of non-limiting example, a communication action may be as simple as denying access to a user based on the assessment that this is not a legitimately authenticated user or it may be the rearrangement of communications services on behalf of a clinician, based upon where that clinician is, who they are with or what they are doing. Other examples of a communication action may include the following:

initiating a communication (e.g., forming a Code Blue team, initiating a session between clinicians, etc.);
    modifying a new or an ongoing communication;
    terminating an ongoing communication; and
    blocking an attempt to establish a communication (e.g., blocking access to files where permissions are inappropriate, etc.).

Another example of a possible outcome of the decision making engine 312 is a decision to modify sensor capabilities or trigger actuators 324. Where the healthcare facility is a hospital, for example, closed loop control might focus security cameras on an event, or lock doors.

A further example of a possible outcome of the decision making engine 312 is a decision to change a parameter that is used as an input by another service. This creates an inter-relatedness among the services being provided by the ECAS 12, which is discussed later on in this specification.

In addition, the decision making engine 312 may also implement an analysis and reporting agent 320 that records the various decisions taken.

Figure 5:
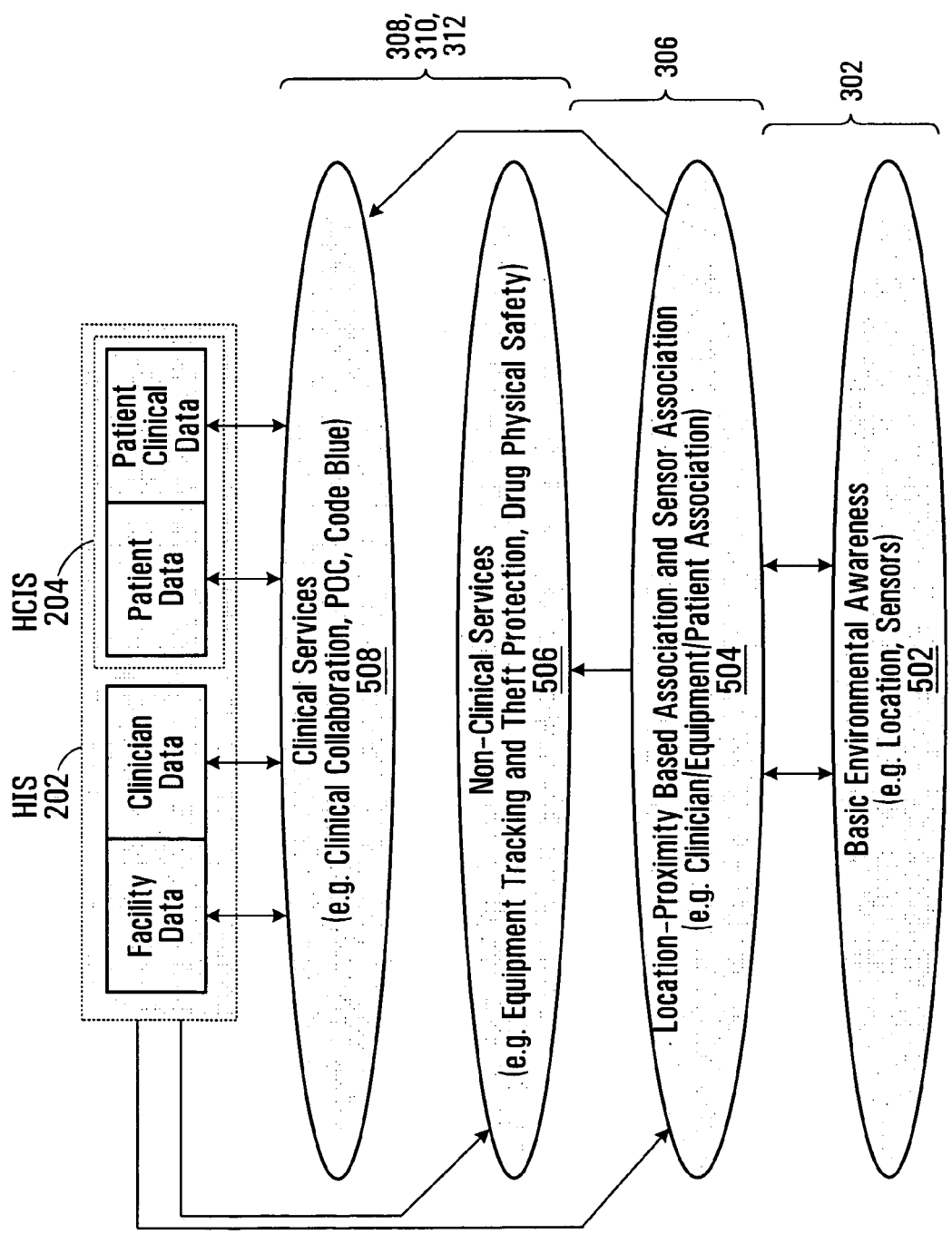
FIG. 5 depicts how the services can be broken down into categories.

In operation, different services are provided by the ECAS 12. These services are interrelated and, for example, can be categorized as clinical or non-clinical, as well as routine or emergency. Reference is made to FIG. 5, for example, which provides a complementary view of the ECAS 12 to that of FIG. 3. Specifically, at layer 502, individual services being provided by the ECAS 12 are associated with detection by the sensor arrangement 302 of activity relevant to the provision of each particular service, thereby to generate sensed data. At layer 504, the environmental context processing engine 306 provides location- and proximity-based association and sensor association by transforming the sensed data (which has been sensed as a result of the activity) into data indicative of an environmental context in which the activity is deemed to have occurred. The data indicative of the environmental context is processed in a specific way, depending on whether the service is clinical (layer 506) or non-clinical (layer 508). In either case, generally speaking, the situational context processing engine 308 transforms the data indicative of the environmental context into data indicative of a situational context in which the activity is deemed to have occurred. The decision making engine 312 then applies data indicative of an institutional context to the data indicative of the situational context in order to determine an action to be taken in accordance with provision of the service. In order to obtain the data indicative of the institutional context, the data indicative of the situation is fed to the institutional context processing engine 310, which then determines, based additionally on knowledge of the particular service (which includes knowledge of whether the service is clinical or non-clinical), appropriate data to retrieve from the HIS 202, HCIS 204, and radiology system 206 such as policies, etc. The decision making engine 312 implements coordination and processing functions, associated with a set of policies, which modifies the behavior of the pervasive access and communication system 208 by applying the decisions back into the components of the ECAS 12.

Figure 6A:
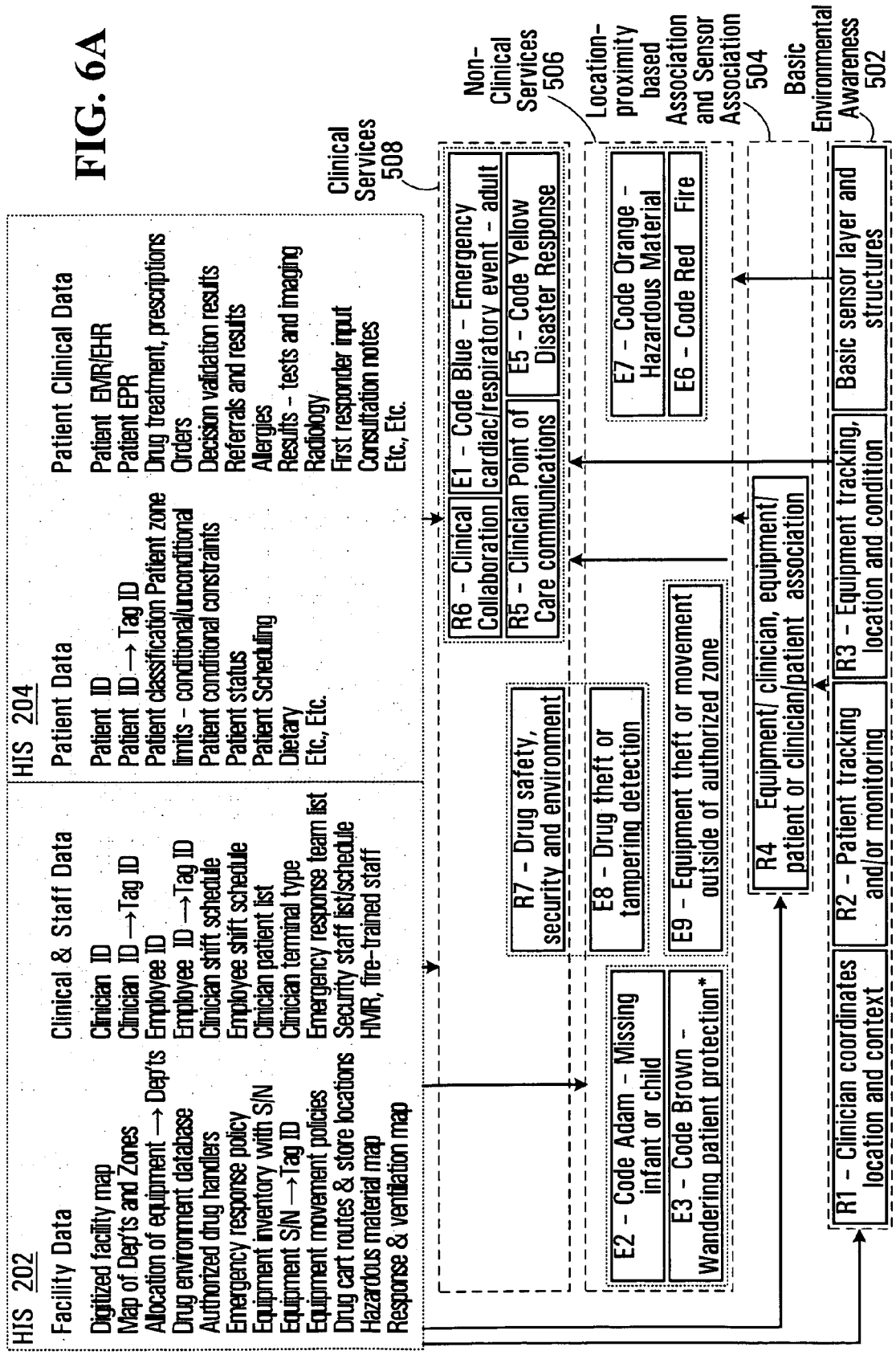
FIGS. 6A and 6B shows an interrelation among the services from a layered services and information flow perspective
Figure 6B:
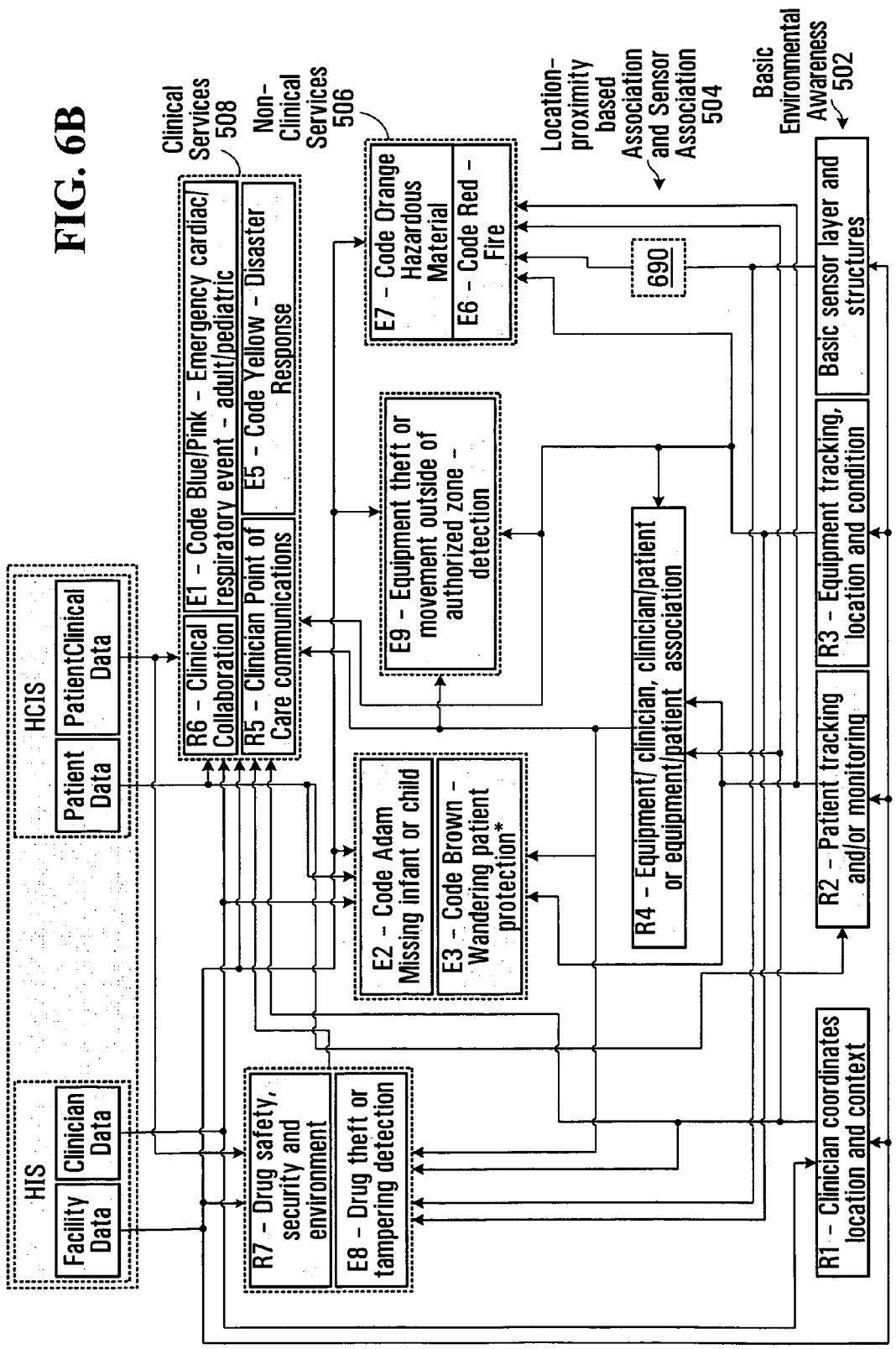

FIGS. 6A and 6B show inter-relationships between representative subsets of routine and emergency clinical services, from a layered services and information flow perspective. At the head of FIG. 6B are the HIS 202 and HCIS 204. Omitted for reasons of space is the Radiology Department 206—although it should be appreciated that the Radiology Department 206 may be treated similarly to HCIS 204 since it too contains a plethora of patient identifiable clinical records. Under the HIS 202 and the HCIS 204 is the clinical layer 508 with some grouped examples of services shown. These communicate with the HIS 202, the HCIS 204 and the environmental layers 502, 504 below them. The non-clinical layer 506, also with some grouped examples of services shown, communicates with the HIS 202 and the environmental layers below them. The basic environmental layers 502, 504 receive mapping, zoning and institution data from the HIS 202 and provide environmental input into the services at the clinical and non-clinical layers 506, 508 above them.

The clinical services layer 508 includes examples of services that are given as "E1 CODE BLUE/PINK-EMERGENCY CARDIAC/RESPIRATORY EVENT-ADULT/PEDIATRIC", which is associated with "R6—CLINICAL COLLABORATION" and "R5—CLINICIAN POINT OF CARE COMMUNICATIONS". All of these are associated with "E5—CODE YELLOW—DISASTER RESPONSE". These are associated because they share many of the same requirements, functions, attributes and information flow and connectivity requirements. Furthermore they should all present their clinical information to the end user in the same manner and have similar user profiles, although the circumstances for their use may be quite different.

Underneath the clinical services layer 508 is shown the non-clinical services layer 506. These may be services which, although not clinical services in themselves, provide vital direct support to clinical services or they may be services separate from clinical services. All of the examples shown are, in fact, emergency services although this will not always be true and some of the emergency services shown in FIGS. 6A and 6B also have non-emergency equivalent services— for instance "E9—EQUIPMENT THEFT OR MOVEMENT OUTSIDE OF AUTHORIZED ZONE" has a routine counterpart, not shown in FIGS. 6A and 6B, for routine equipment tracking and accessing for maintenance/calibration purposes or for locating (inventory control) before a routine clinical procedure or even for an annual audit. The services shown as "E7—CODE ORANGE—HAZARDOUS MATERIAL RELEASE" and "E6—CODE RED—FIRE" have substantial commonalities, both being involved in evacuating part or all of the building, understanding the extent and spread of the fire and smoke or products from the hazardous material and identifying people and equipment at risk in the vicinity as well as helping provide data to coordinate the containment and elimination of the threat.

For the same reason—namely, commonality of form and function—"E2—CODE ADAM—MISSING INFANT OR CHILD" and "E3—CODE BROWN—WANDERING/LOST PATIENT" can be grouped. Similarly, "E8—DRUG THEFT OR TAMPERING DETECTION" and "R7—DRUG SAFETY, SECURITY AND ENVIRONMENT" can also be associated. This pair are shown placed slightly higher in FIGS. 6A and 6B than the others since R7 would have a clinical component to it if the drug safety and tracking the whereabouts of the drugs is extended through to patient administration in which case an extension of this service can provide drug dosage verification, although this is not shown in FIGS. 6A and 6B.

Below the non-clinical services layer 506 are shown some of the basic Environmental Awareness layer 502 and Location- and Proximity-Based and Sensor Association layer 504, which provide support services, of which only "R4—EQUIPMENT/CLINICIAN, CLINICIAN/PATIENT OR EQUIPMENT/PATIENT ASSOCIATION" is shown. Sensor association services are not explicitly shown in FIG. 6B but would occupy the area denoted by reference numeral 690. The lines between the individual services or dotted groupings of services represent the most significant identified linkages between them. These linkages, in terms of input and output information will be detailed in the following sections as part of the discussions around the functionality of each of the services.

Figure 7A:
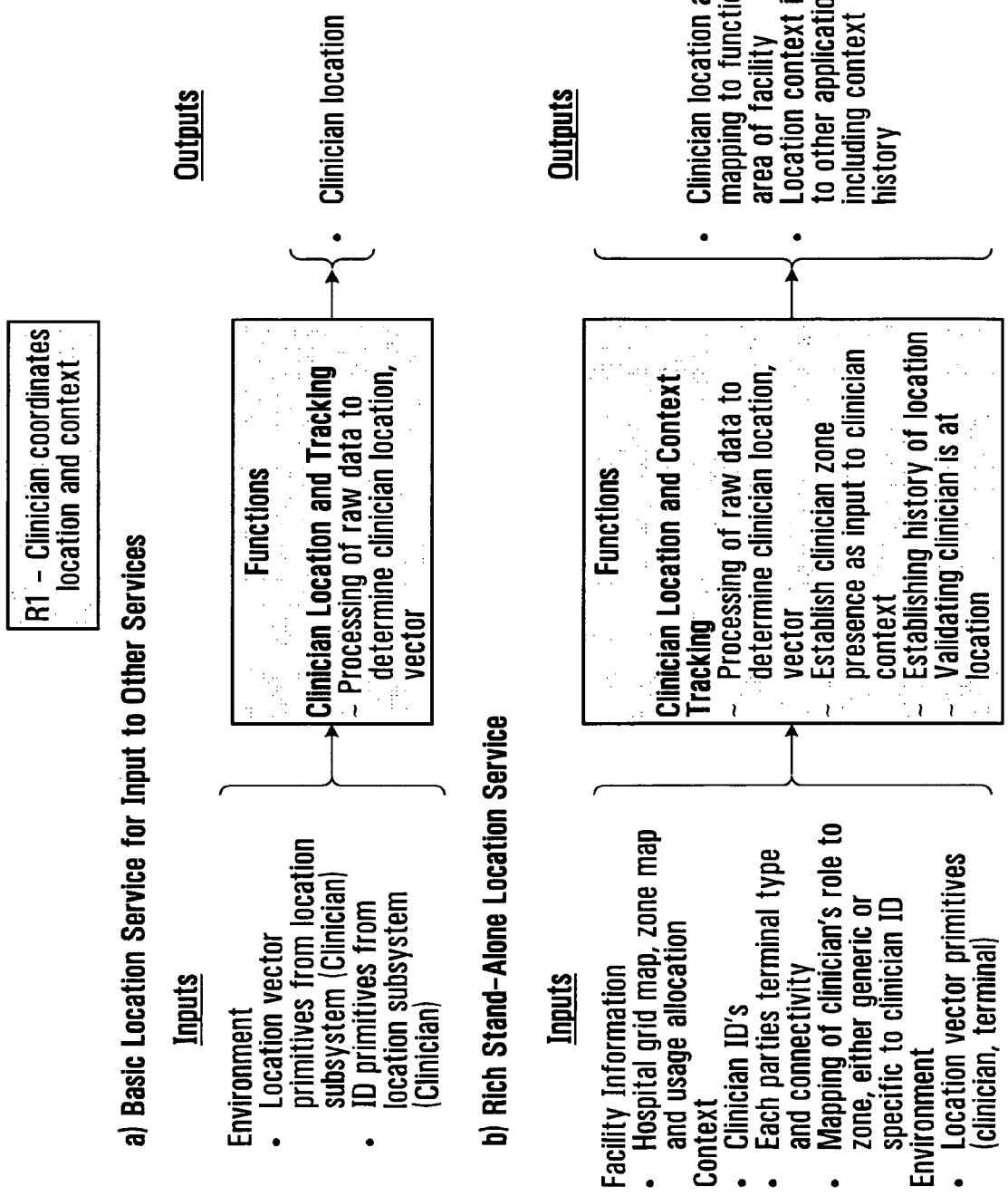
FIGS. 7A through 7O illustrate inputs, outputs and functionality of individual ones of the services that can be provided by the environment- and context-aware system.
Figure 7B:
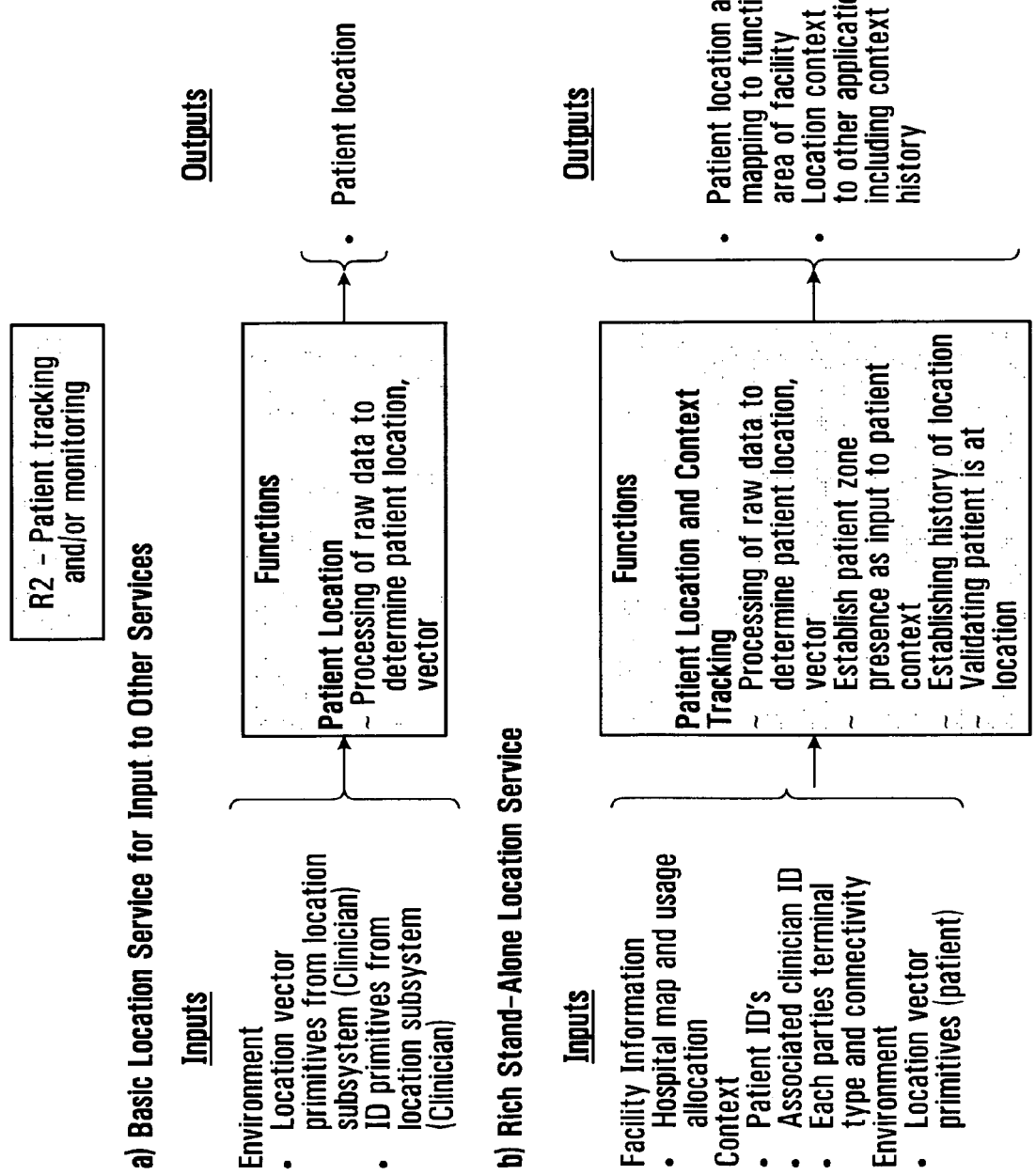
Figure 7C:
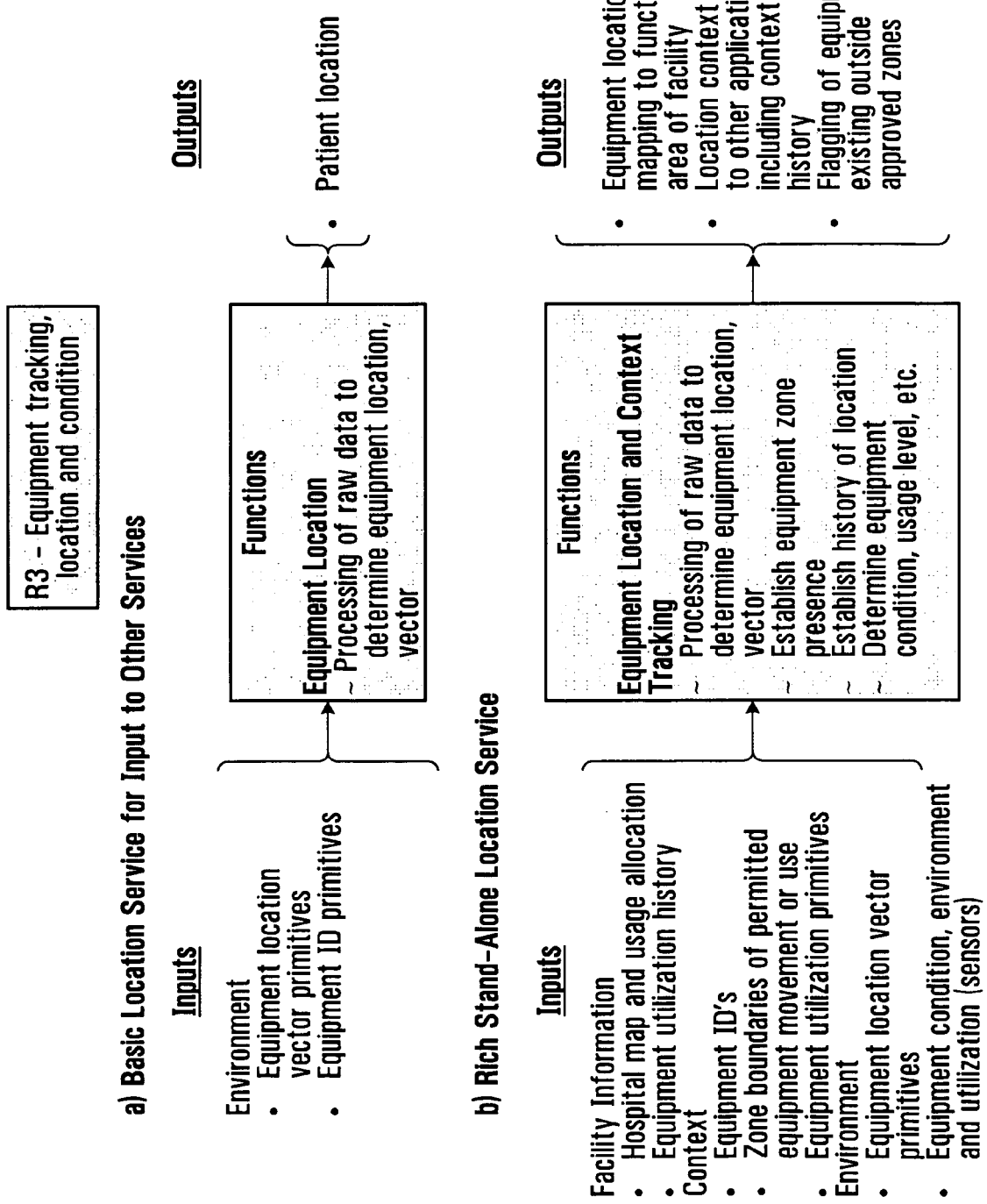
Figure 7D:
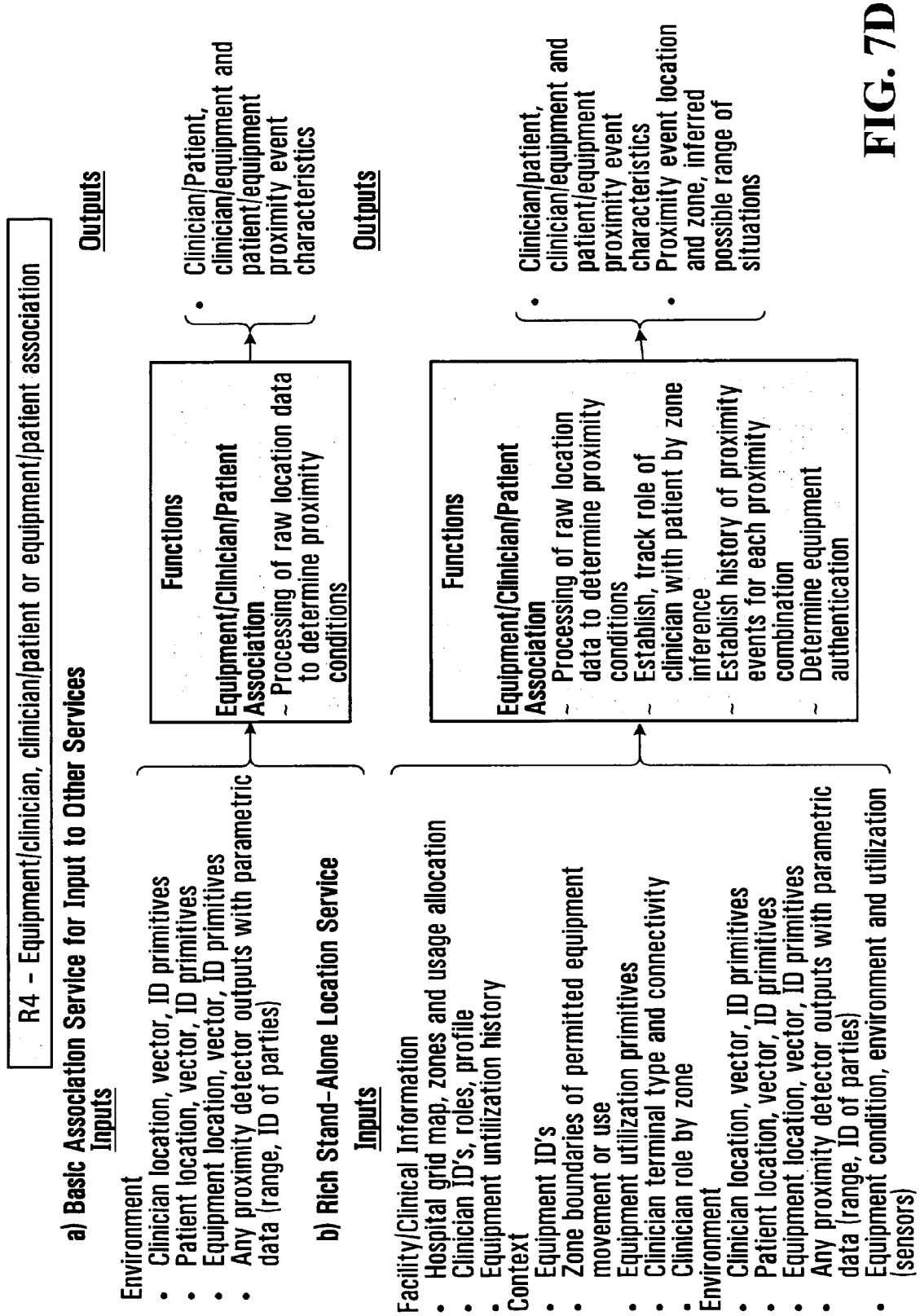
Figure 7E:
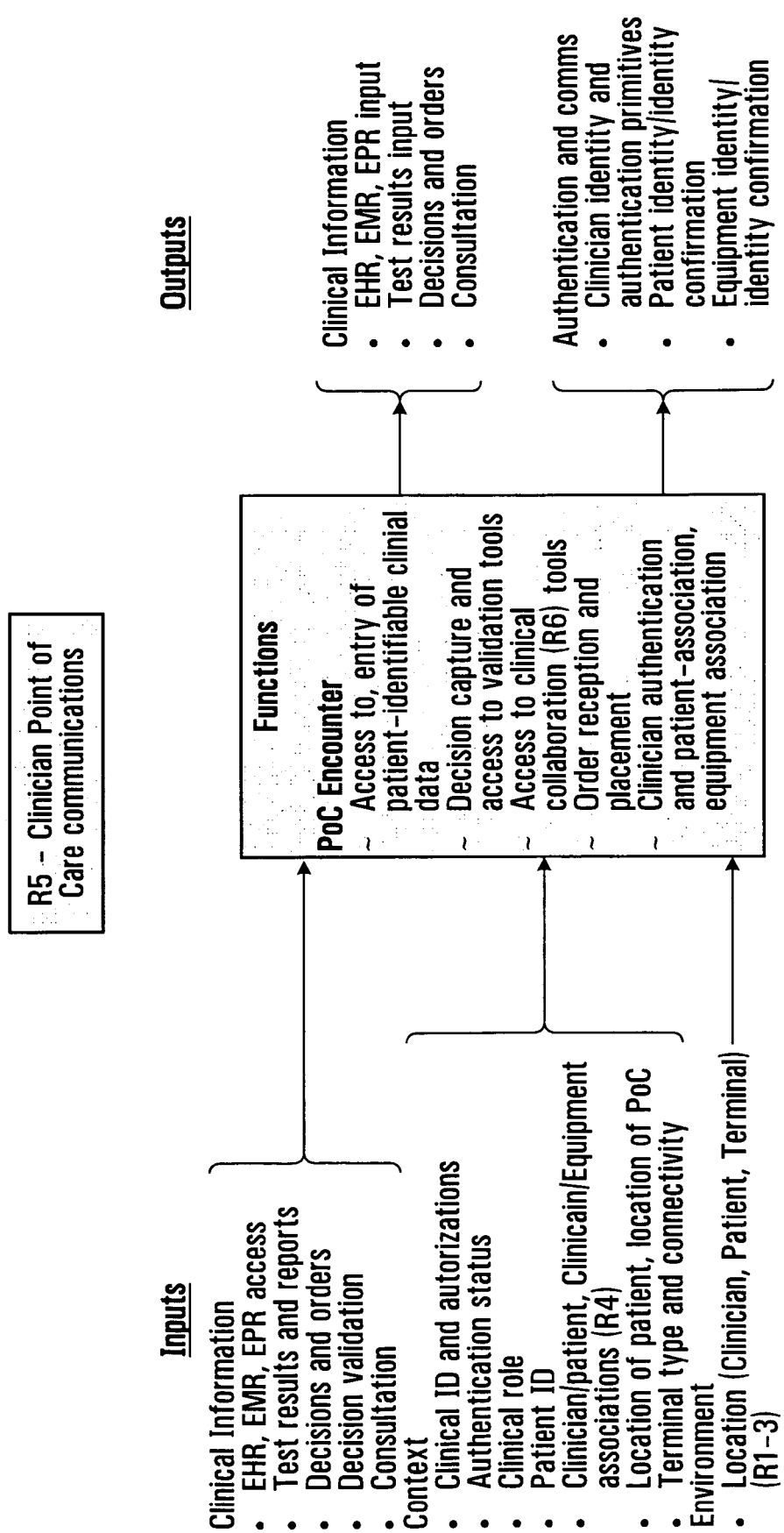
Figure 7F:
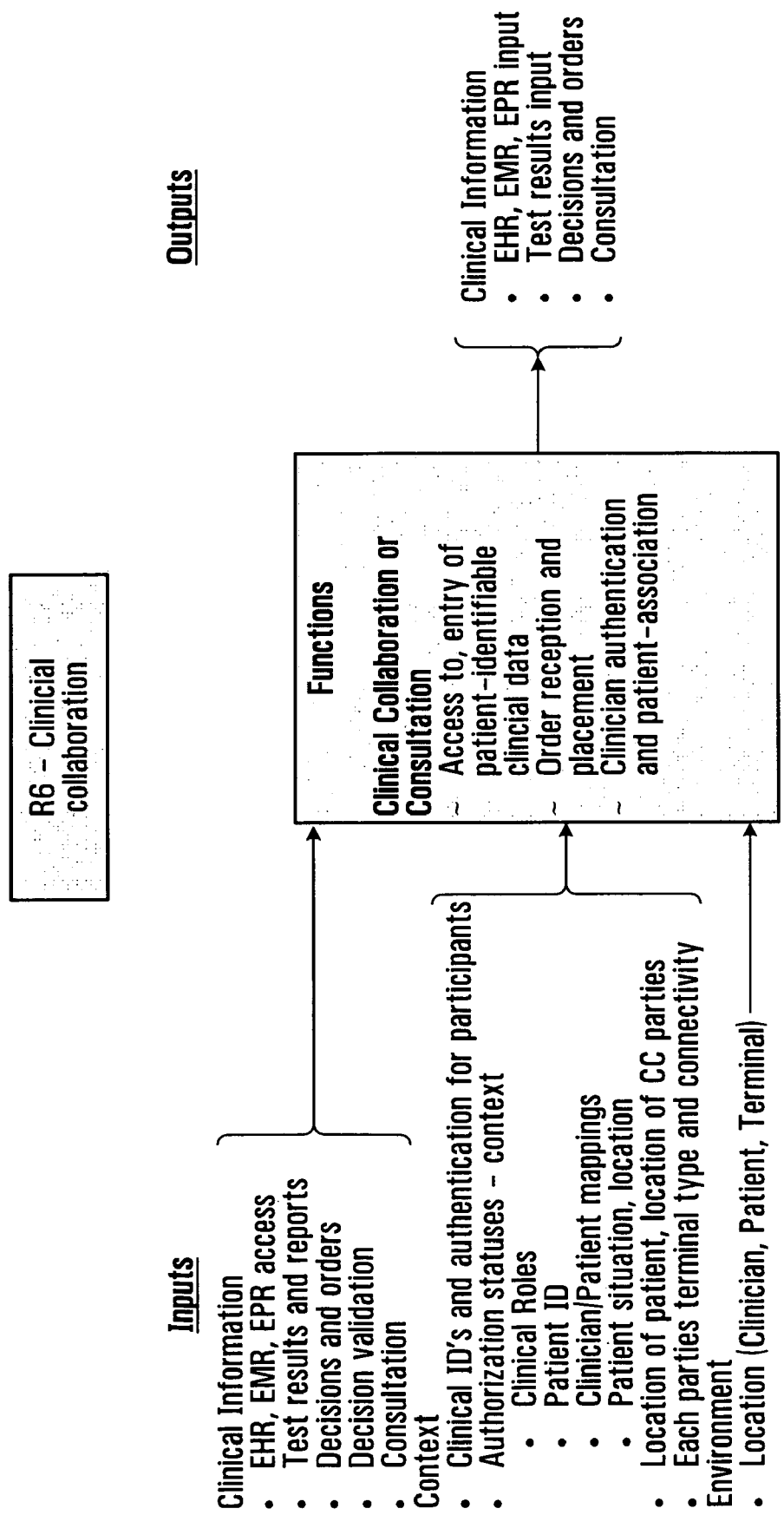
Figure 7G:
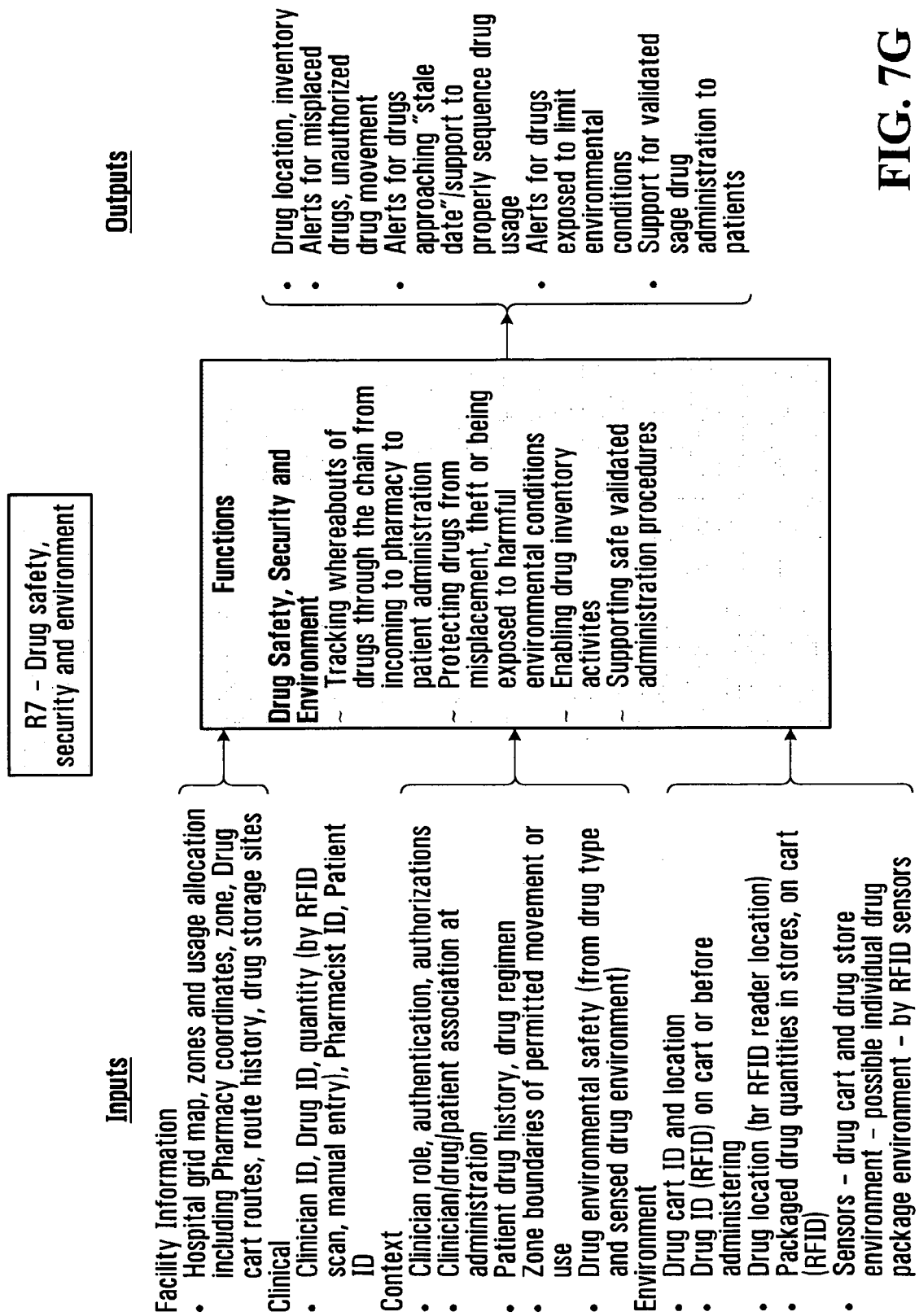
Figure 7H:
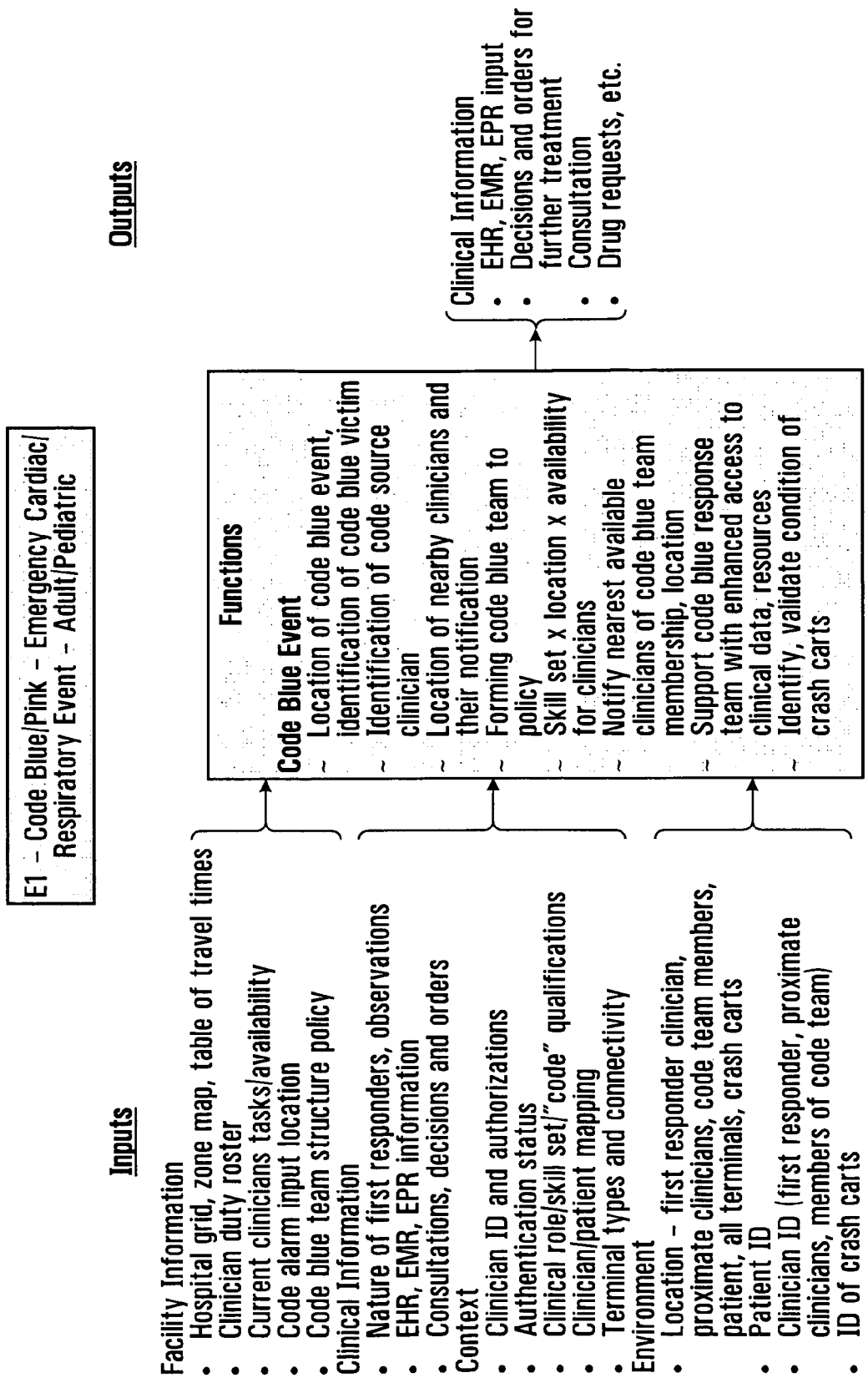
Figure 7I:
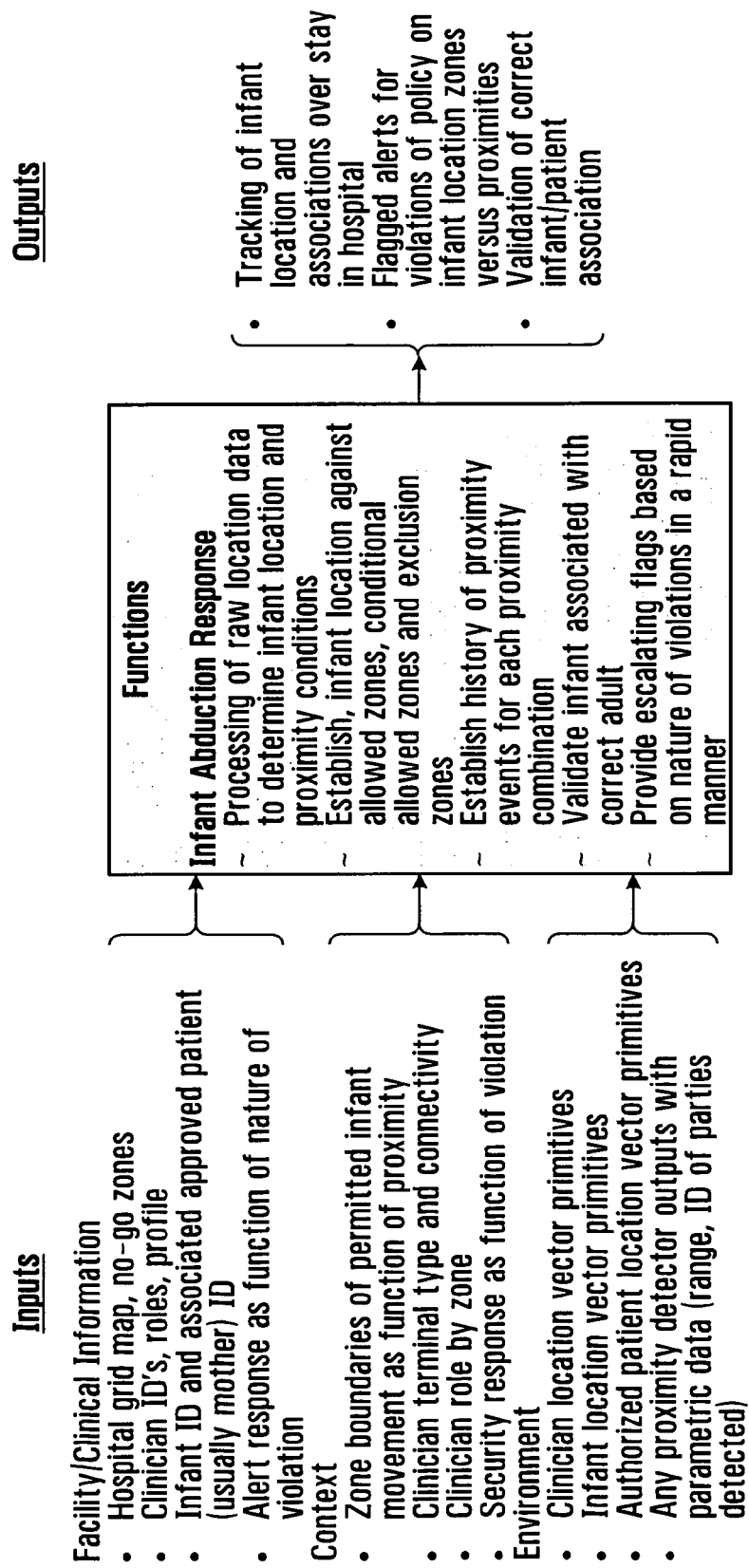
Figure 7J:
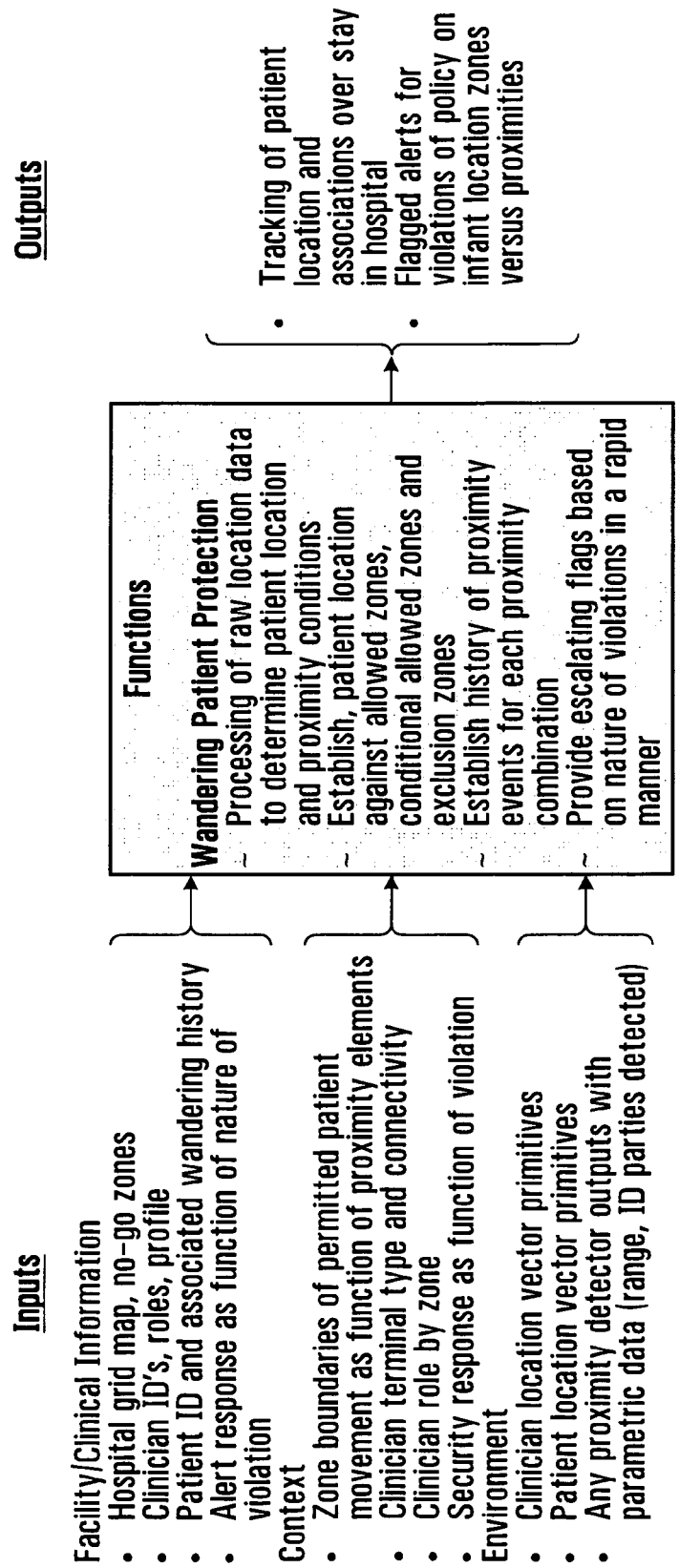
Figure 7K:
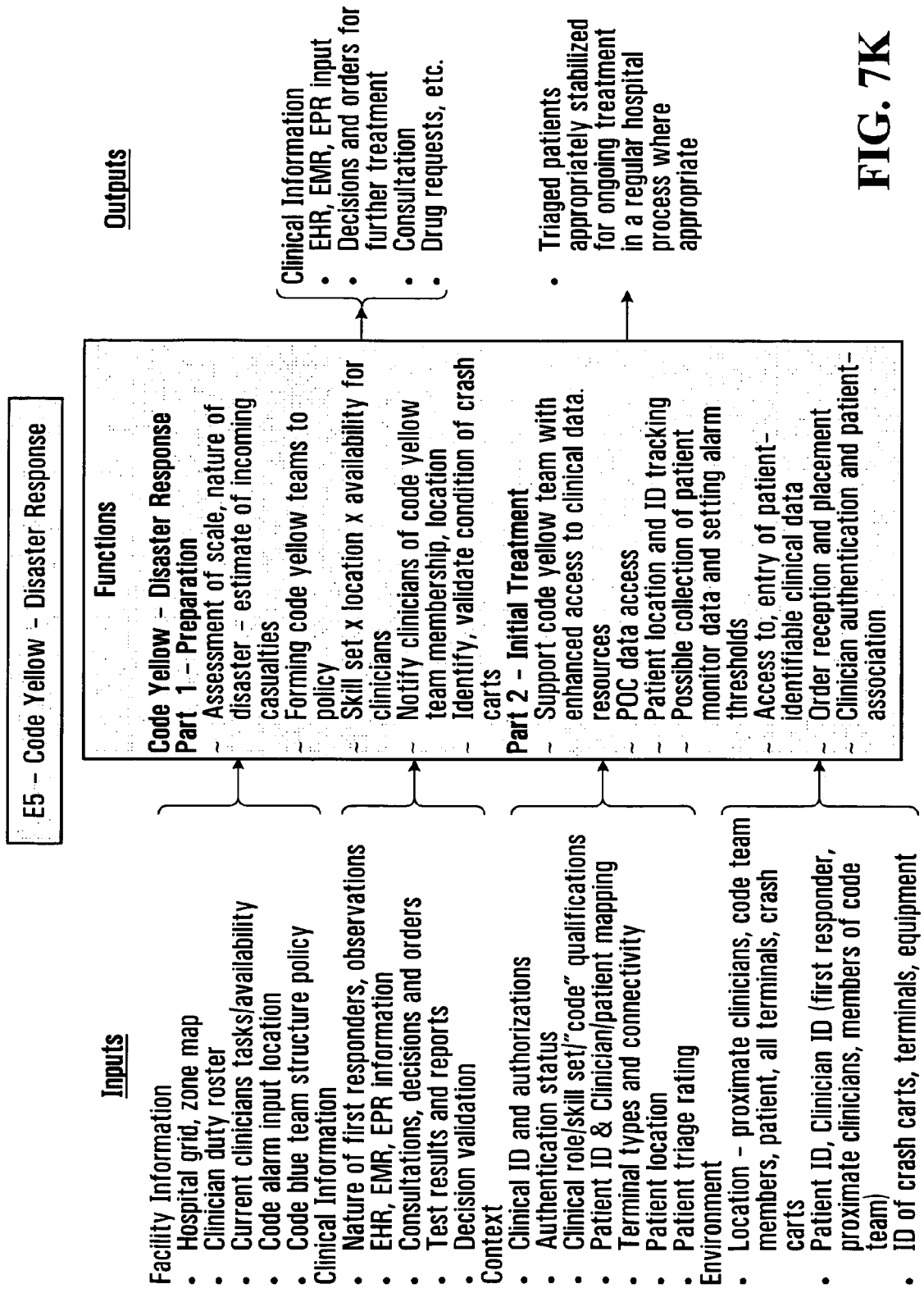
Figure 7L:
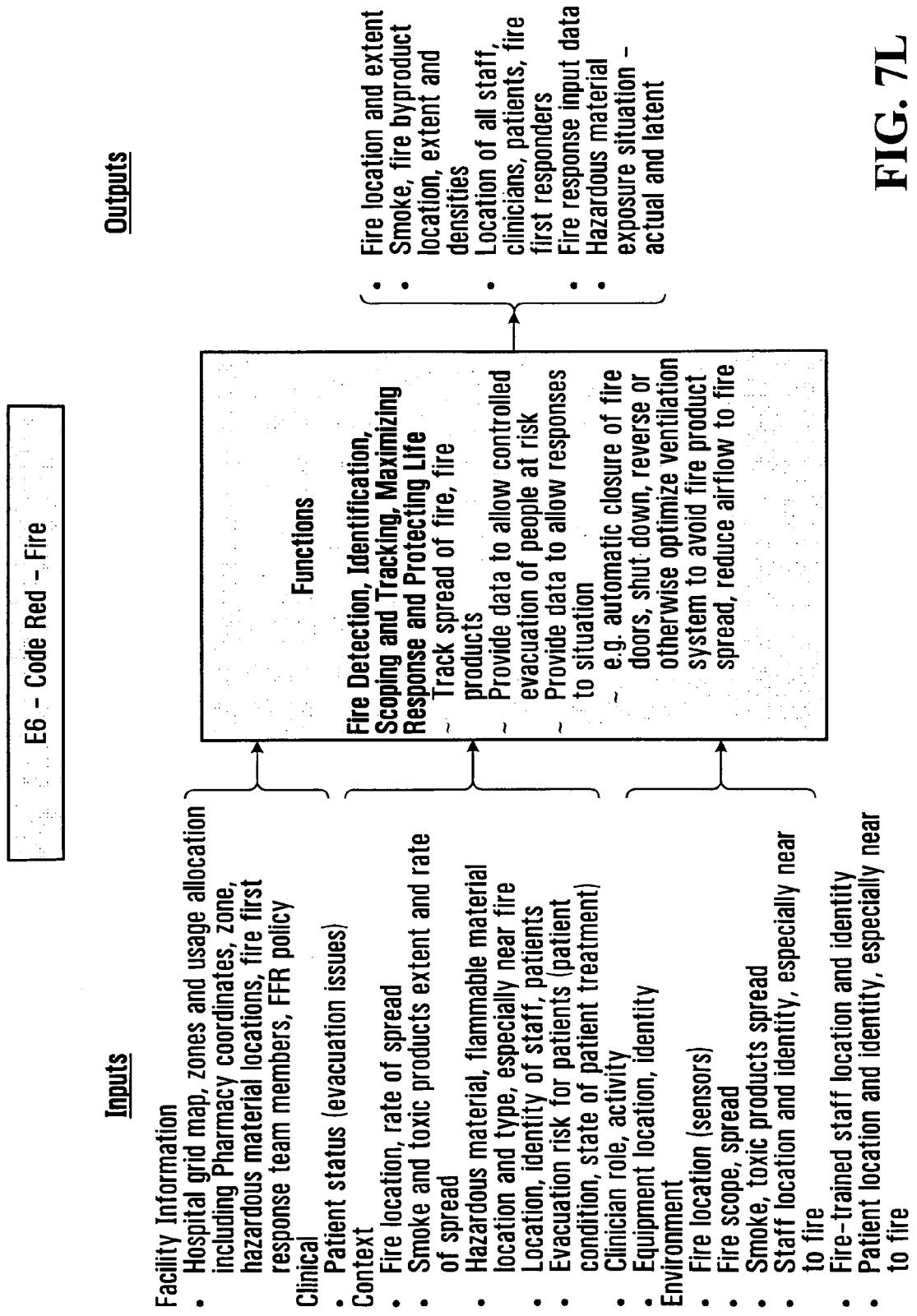
Figure 7M:
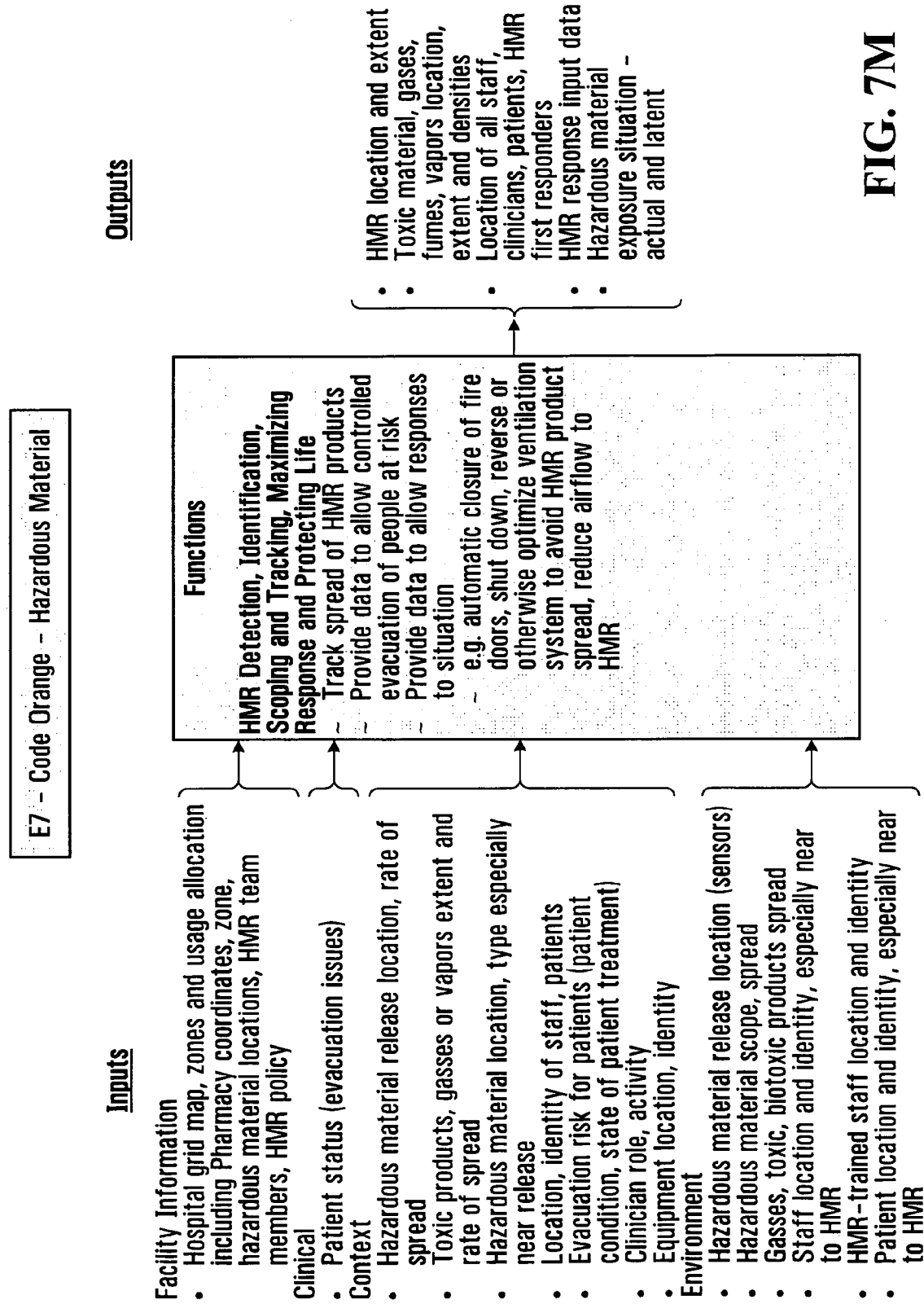
Figure 7O:
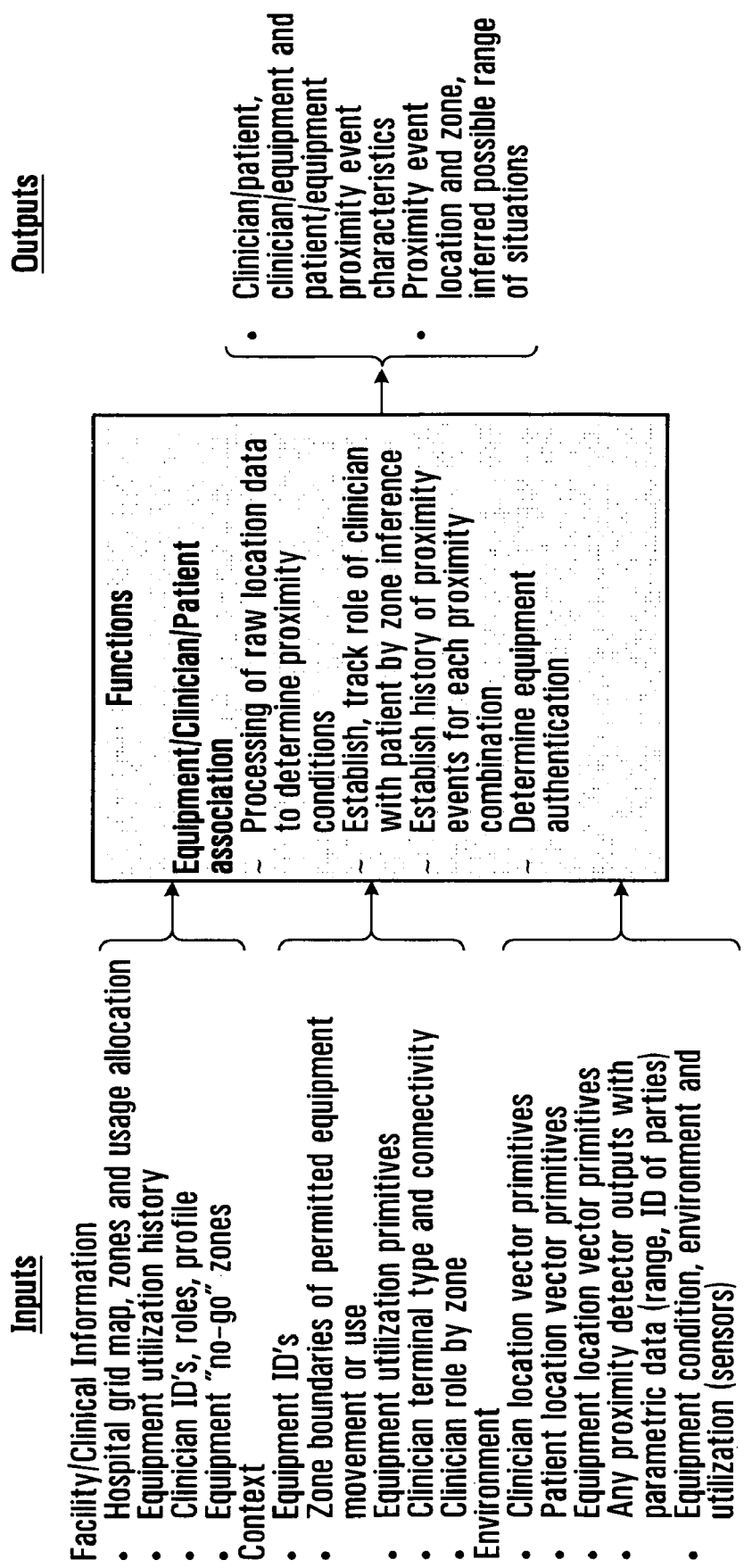

It is useful to consider an incomplete but broadly representative example set of services and to categorize them in terms of some basic commonalities and also to describe their interrelatedness. Accordingly, reference is made to FIGS. 7A through 7O, which illustrate the inputs, outputs and functionality of individual ones of the services.

With reference now to FIG. 8, there are shown example quantitative requirements for four (4) specific services that were taken to a deeper level of analysis, namely (i) "R2—EQUIPMENT TRACKING, LOCATION AND MONITORING"; (ii) "R5—POINT OF CARE COMMUNICATIONS" walking through a clinician-patient encounter; (iii) "E1—AUTOMATED FORMATION OF A CODE BLUE TEAM"; and (iv) "E2—CODE ADAM". It should be appreciated that the quantitative requirements shown in FIG. 8 should be taken as merely illustrative of the ability of the ECAS 12 to provide complex services of high value.

Thus, to summarize, the environmental context processing engine 306 can understand the physical environment it is being used in, while the situational context processing engine 308 determines the situation in which the sensed or detected activity is deemed to occur. The institutional context processing engine 310 identifies relevant policies, permissions, authentications, resource maps and lists, etc. pertaining to the situation and feeds them to the decision making engine 312 where they are applied, resulting in conclusions being made and actions (such as communication actions) being taken based on those conclusions.

As a result, the ECAS 12 provides an ability to determine a situation occurring in a clinical workflow or a series of clinical workflows and appropriately modify communications to and from those clinical workflows, such modifications being in accordance with facility policies, procedures and other guiding or reference information. The situation is determined based on an environmental sensing capability, such that the workflow situation can be deduced at least partially from that environmental sensing capability. To this end, the ECAS 12 comprises the environmental context processing engine 306, the situational context processing engine 308 and the institutional context processing engine 310.

Also, it should be appreciated that although the environmental context processing engine 306, the situational context processing engine 308 and the institutional context processing engine 310 may each be composed of multiple sub-engines that interact with one another. In some cases, the sub-engines of a particular context processing engine may be relatively similar and thus provide a collectively enhanced processing power. In other cases, the sub-engines of a particular context processing engine may be different and indeed focused on executing different processing functions. For example, one environmental context processing sub-engine may be focused on inventory/location/asset tracking while another environmental context processing sub-engine may be focused on chemicals, gases, radiation. Together (and with other sub-engines) they help provide a coherent view of the entire picture. A similar approach can be applied to the situational context processing engine 308 and the institutional processing engine 310, whose sub-engines may have certain distinct processing functions (e.g., focusing on building operations vs. clinicians) as well as certain other processing functions that are common (e.g., an overarching response to a natural disaster).

It should thus be appreciated that by implementing its functionality, the ECAS 12 is able to provide the following benefits:

matching the communication format to the needs and abilities of the user situation—for instance a clinician who is a senior physician dealing with an emergency clinical situation may have different communications requirements than a junior nurse doing routine patient checks; or for instance modifying the display for a privacy mode or changing the format of the information to have less detail but more relevant information in an emergency situation;

matching the communication structure to the capabilities of the end user device—for instance a clinician using a large screen tablet Personal Computer (PC) may receive data in a graphical or image form while another clinician using a small screen PDA would receive the same data in a different form, perhaps several pages of text or tables;

assessing the overall situation and modifying communications content appropriately—for instance a physician accessing a Point-of-Care (PoC) system while with a particular patient (i.e., in proximity to that patient) may be guided preferentially to the records for that patient instead of having to find them;

assessing the authentication status and terminal/personnel association status and modifying re-authentication requirements appropriately—for instance if a clinician is authenticated to his or her tablet PC and the tablet PC is tracked as traveling through the healthcare facility with the clinician then it remains an authenticated device but should the clinician and the tablet PC become non-proximate for a period of time then a policy is applied that eventually leads to suspending or terminating authentication. Should the tablet PC start traveling a significant distance from the clinician then its authentication becomes suspended or terminated immediately.

identifying appropriate physical world parameters, deriving the situation and either initiating or modifying communications as a result—as an example when a tablet PC or other piece of equipment is detected as traveling out of its approved zone, based on organization policies then appropriate action can be taken. As an example, a tablet PC, normally proximate to a specific clinician may be detected traveling through the healthcare facility without a continuously proximate clinician—in that circumstance the application of policy may determine that the device is likely being stolen, since all employees can be tracked and no-one is being tracked with this device, and appropriate security or theft prevention protocols can be activated.

Those skilled in the art will appreciate that the functionality of the ECAS 12 can be overlaid in stages on top of an existing infrastructure, albeit with some adaptation of that infrastructure. This can be implemented all at once for a massive change in capabilities or can be carried out in stages, for instance making the necessary connections within the core databases to allow the addition of a situational context processing engine, prior to overlaying a staged roll-out of an environmentally aware capability. As an example, a staged approach may involve adding location software to the WLAN, then adding a sensor capability, then upgrading the location solution to a precision location solution to allow real-time equipment-personnel and personnel-personnel associations, to add various stages and levels of functionality as required.

Those skilled in the art will also appreciate that the present invention is not limited to the healthcare facility that has been used as an example in the above description. Rather, the ECAS 12 has application to any type of healthcare facility that can take on a diversity of forms, including a hospital, a clinic, a doctor's office, a home care facility, a nomadic point of care and a mobile ambulance, to name a few non-limiting possibilities. In fact, it should be appreciated that aspects of the present invention are applicable outside the healthcare realm.

While specific embodiments of the present invention have been described and illustrated, it will be apparent to those skilled in the art that numerous modifications and variations can be made without departing from the scope of the invention as defined in the appended claims.

What is claimed is:

1. A system for providing a service in an institutional setting, the system comprising:
   an environmental context processing engine configured to transform sensed data indicative of activity relevant to provision of said service into data indicative of an environmental context in which said activity is deemed to have occurred;
   a situational context processing engine configured to transform the data indicative of the environmental context into data indicative of a situational context in which said activity is deemed to have occurred; and
   a decision making engine configured to apply data indicative of an institutional context to the data indicative of the situational context in order to determine an action to be taken in accordance with provision of said service.

2. The system defined in claim 1, wherein said activity comprises movement of at least one of: a patient, a clinician and an object.

3. The system defined in claim 1, wherein the sensed data comprises identification data from at least one of: an RFID tag, a WLAN tag and a UWB tag.

4. The system defined in claim 1, wherein the sensed data comprises location data from at least one of: an RFID tag, a-WLAN tag and a UWB tag.

5. The system defined in claim 1, wherein the sensed data comprises data output by at least one medical instrument.

6. The system defined in claim 1, further comprising:
   a sensor arrangement disposed throughout the institutional setting, said sensors configured to produce the sensed data.

7. The system defined in claim 6, wherein the sensors comprise at least one of a proximity sensor and a location sensor.

8. The system defined in claim 6, wherein the sensors comprise at least one of: a location, tracking or proximity sensor, a camera, a clinical sensor, a sound sensor, a vibration sensor, a movement sensor, a visible light sensor, an infra-red light sensor, a wireless signal sensor, a mass/weight/pressure sensor, a chemical sensor, a biotoxin sensor, a hard radiation sensor, a liquids/fluids/water sensor and a gas/vapour sensor.

9. The system defined in claim 6, further comprising a sensor backhaul network configured to convey the sensed data from the sensor arrangement to the environmental context processing engine.

10. The system defined in claim 6, further comprising a plurality of actuators, wherein said action includes control of at least one of said actuators.

11. The system defined in claim 10, wherein the at least one of said actuators is configured to activate a corresponding one of said sensors.

12. The system defined in claim 10, wherein the at least one of said actuators is configured to cause a corresponding one of said sensors to effectuate a self-test.

13. The system defined in claim 1, wherein the data indicative of the environmental context in which said activity is deemed to have occurred comprises information associated with a state of an environment in which said activity is deemed to have occurred, the data indicative of the situational context in which said activity is deemed to have occurred comprises information associated with a circumstance surrounding said activity, and the data indicative of the institutional context comprises policies and procedures of the institutional setting that are associated with provision of said service.

14. The system defined in claim 1, wherein the environmental context processing engine implements a plurality of environment-plane processing functional units, each configured to process the sensed data from a subset of said sensors that are active in the respective environment-plane.

15. The system defined in claim 14, wherein the plurality of environment-plane processing functional units are implemented as virtualized functions co-located in a single physical machine.

16. The system defined in claim 14, wherein the plurality of environment-plane processing functional units are located in respective physical machines.

17. The system defined in claim 1, wherein the environmental context processing engine implements a localization function that combines sensed data from multiple location receivers to pinpoint a location of a patient, clinician or object.

18. The system defined in claim 17, wherein the environmental context processing engine further implements sensor collection, processing and encapsulation.

19. The system defined in claim 17, wherein the environmental context processing further implements a sensor system virtualization function.

20. The system defined in claim 1, further comprising an institutional context processing engine configured to consult an institution information system based on the data indicative of the situational context, thereby to obtain the data indicative of the institutional context.

21. The system defined in claim 20, wherein the data indicative of the institutional context comprises at least some information obtained from a healthcare clinical information system.

22. The system defined in claim 21, wherein the information obtained from the hospital clinical information system comprises one or more of: policies; lists of entities; patient medical status; patient test data; patient schedule data; patient-clinician association data; EHR data; EMR data; EPR data; ordered patient treatment data; diagnosis data; prognosis data; staff skills lists; and duty rosters.

23. The system defined in claim 20, wherein the data indicative of the institutional context comprises at least some information obtained from a hospital non-clinical information system.

24. The system defined in claim 23, wherein the information obtained from the hospital non-clinical information system comprises at least one of: financial data, building maintenance schedule data, clinician accreditation data, clinician rights and privileges data, clinician work schedule data and clinician IT preference data.

25. The system defined in claim 20, wherein the data indicative of the institutional context comprises at least some information obtained from a radiological system.

26. The system defined in claim 1, wherein to transform the data indicative of the environmental context into the data indicative of the situational context, the situational context processing engine is configured to process indications of communication activity received from a pervasive access and communication system.

27. The system defined in claim 26, wherein said action comprises a communication action, wherein said decision making engine is further configured to instruct said pervasive access and communication system to take said action.

28. The system defined in claim 27, wherein said action comprises a communication action, wherein said decision making engine is further configured to instruct a data flow adaptation module operatively coupled to said pervasive access and communication system to take said action.

29. The system defined in claim 27, wherein said communication action comprises an action to initiate a communication session over said pervasive access and communication system.

30. The system defined in claim 27, wherein said communication action comprises an action to modify a communication session ongoing over said pervasive access and communication system.

31. The system defined in claim 27, wherein said communication action comprises an action to terminate a communication session ongoing over said pervasive access and communication system.

32. The system defined in claim 27, wherein said communication action comprises an action to block an attempt to establish a communication over said pervasive access and communication system.

33. The system defined in claim 26, wherein said indications of communication activity comprise communications presence data.

34. The system defined in claim 33, wherein said indications of communication activity further comprise device type, device capabilities, bandwidth usage, service type, session type and entity status.

35. The system defined in claim 1, wherein said decision making engine is further configured to take said action.

36. The system defined in claim 1, further comprising at least one management entity operatively coupled to the context processing engines, the at least one management entity being configured to allow a user to configured or reconfigure operation of the context processing engines.

37. The system defined in claim 1, wherein the institutional setting comprises a healthcare facility.

38. The system defined in claim 1, wherein the situational context processing engine implements a plurality of situational context processing sub-engines.

39. The system defined in claim 38, wherein the plurality of situational context processing sub-engines are implemented as virtualized functions co-located in a single physical machine.

40. The system defined in claim 38, wherein the plurality of situational context processing sub-engines are located in respective physical machines.

41. The system defined in claim 1, wherein the institutional context processing engine implements a plurality of institutional context processing sub-engines.

42. The system defined in claim 41, wherein the plurality of institutional context processing sub-engines are implemented as virtualized functions co-located in a single physical machine.

43. The system defined in claim 41, wherein the plurality of institutional context processing sub-engines are located in respective physical machines.

44. A method for providing a service in an institutional setting, the method comprising:
    obtaining sensed data indicative of activity relevant to provision of said service;
    transforming said sensed data into data indicative of an environmental context in which said activity is deemed to have occurred;
    transforming the data indicative of the environmental context into data indicative of a situational context in which said activity is deemed to have occurred; and
    applying data indicative of an institutional context to the data indicative of the situational context in order to determine an action to be taken in accordance with provision of said service.

45. A system for providing a service in an institutional setting, the system comprising:
    means for obtaining sensed data indicative of activity relevant to provision of said service;
    means for transforming said sensed data into data indicative of an environmental context in which said activity is deemed to have occurred;
    means for transforming the data indicative of the environmental context into data indicative of a situational context in which said activity is deemed to have occurred; and
    means for applying data indicative of an institutional context to the data indicative of the situational context in order to determine an action to be taken in accordance with provision of said service.

46. A method implemented in a healthcare facility, the method comprising:
- collecting sensed data relevant to a clinical workflow;
- detecting a situation occurring in the clinical workflow based on the sensed data;
- determining a state of an environment associated with the situation based on the sensed data;
- determining an institutional context based on the situation; and
- modifying communications to and from the clinical workflow based on the detected situation, the state of the environment associated with the situation, and the institutional context, wherein the communications are modified at least in partial accordance with facility policies and procedures.

47. The method defined in claim 46, wherein collecting the sensed data and determining the state of the environment is performed by an environmental context processing engine.

48. The method defined in claim 46, wherein the detecting is performed by a situational context processing engine.

49. The method defined in claim 48, wherein determining the institutional context is performed by an institutional context processing engine.

* * * * *